United States Patent [19]
Sugimoto et al.

[11] Patent Number: 5,919,694
[45] Date of Patent: Jul. 6, 1999

[54] MUTANT PHOSPHOENOLPYRUVATE CARBOXYLASE, ITS GENE, AND PRODUCTION METHOD OF AMINO ACID

[75] Inventors: Masakazu Sugimoto; Tomoko Suzuki; Hiroshi Matsui, all of Kawasaki; Katsura Izui, Kyoto, all of Japan

[73] Assignee: Ajinomoto Co., Inc., Tokyo, Japan

[21] Appl. No.: 08/967,104

[22] Filed: Nov. 10, 1997

Related U.S. Application Data

[62] Division of application No. 08/596,366, filed as application No. PCT/JP94/01365, Aug. 17, 1994.

[30] Foreign Application Priority Data

Aug. 24, 1993 [JP] Japan ................................. 5-209775
Aug. 24, 1993 [JP] Japan ................................. 5-209776
Jul. 5, 1994 [JP] Japan ................................. 6-153876

[51] Int. Cl.$^6$ ............................. C07H 21/04; C12N 1/20
[52] U.S. Cl. ................. 435/252.33; 435/252.3; 435/252.32; 435/320.1; 536/23.1; 536/23.2; 536/23.7
[58] Field of Search ............... 435/232, 252.3, 435/252.33, 106, 320.1, 252.32; 536/23.1, 23.2, 23.7

[56] References Cited

U.S. PATENT DOCUMENTS 5,616,480 4/1997 Sugimoto et al. .................... 435/172.3

FOREIGN PATENT DOCUMENTS 0358940 3/1990 European Pat. Off. .

OTHER PUBLICATIONS

Biochem. Biophys. Res. Commun., vol. 45, No. 3, Nov. 5, 1971, pp. 689–694.

J. Biochem., vol. 81, No. 5, 1977, pp. 1473–1485.

J. Biochem., vol. 85, No. 2, Feb. 1979, pp. 423–432.

J. Biochem., vol. 84, No. 4, 1978, pp. 795–803.

Fujita et al. "The primary structure of phosphoenolpyruvate carboxylase of *Escherichia coli*. Nucleotide sequence . . . " J. Biochem. 95, 1984, pp. 909–916.

*Primary Examiner*—Robert A. Wax
*Assistant Examiner*—Nashaat T. Nashed
*Attorney, Agent, or Firm*—Oblon, Spivak, McClelland, Maier & Neustadt, P.C.

[57] ABSTRACT

A phosphoenolpyruvate carboxylase gene, which has mutation such as mutation to replace 625th glutamic acid from the N-terminus of phosphoenolpyruvate carboxylase with lysine, mutation to replace 438th arginine from the N-terminus with cysteine and the like, is introduced into *Escherichia coli* or coryneform bacteria, so as to produce a phosphoenolpyruvate carboxylase which is not substantially inhibited by aspartic acid, thereby amino acid is efficiently produced.

17 Claims, 13 Drawing Sheets

WILD TYPE ENZYME (●)  K650A MUTANT ENZYME (○)
K491A MUTANT ENZYME (□)  K620S MUTANT ENZYME (◇)

MUTANT PHOSPHOENOLPYRUVATE CARBOXYLASE, ITS GENE, AND PRODUCTION METHOD OF AMINO ACID

This is a Division, of application Ser. No. 08/596,366 filed on Apr. 29,1996, now allowed, which was filed as International Application No. PCT/JP94/01365 filed on Aug. 17, 1994.

TECHNICAL FIELD

The present invention relates to a mutant phosphoenolpyruvate carboxylase, a gene coding for it, and a production method of an amino acid, and in particular relates to a gene having mutation to desensitize feedback inhibition by aspartic acid, and utilization thereof.

BACKGROUND ART

Phosphoenolpyruvate carboxylase is an enzyme which is found in almost all bacteria and all plants. The role of this enzyme resides in biosynthesis of aspartic acid and glutamic acid, and supply of C4 dicarboxylic acid to the citric acid cycle for maintaining its turnover. However, in the fermentative production of an amino acid using a microorganisms, there have been few reports on effects of this enzyme has not been made clear (Atsushi Yokota and Isamu Shiio, Agric. Biol. Chem., 52, 455–463 (1988), Josef Cremer et al., Appl. Environ. Microbiol., 57, 1746–1752 (1991), Petra, G. Peters-Weintisch, FEMS Microbial. Letters, 112, 269–274 (1993)).

By the way, the amino acid is a compound which universally exists in cells as components of proteins, however, for the sake of economic energy metabolism and substance metabolism, its production is strictly controlled. This control is principally feedback control, in which the final product of a metabolic pathway inhibits the activity of an enzyme which catalyzes the earlier step of the pathway. Phosphoenolpyruvate carboxylase also undergoes various regulations in expression of its activity.

For example, in the case of phosphoenolpyruvate carboxylase of microorganisms belonging to the genus Corynebacterium or the genus Escherichia, the activity is inhibited by aspartic acid. Therefore, the aforementioned amino acid biosynthesis, in which phosphoenolpyruvate carboxylase participates, is also inhibited by aspartic acid.

In the prior art, various techniques have been developed for efficient production in amino acid fermentation, and fermentative production has been carried out for leucine, isoleucine, tryptophan, phenylalanine and the like by using mutant strains converted to be insensitive to feedback control. However, there has been known neither mutant phosphoenolpyruvate carboxylase converted to be insensitive to inhibition by aspartic acid, nor attempt to utilize it for fermentative production of amino acids of the aspartic acid family and the glutamic acid family.

On the other hand, ppc gene, which is a gene coding for phosphoenolpyruvate carboxylase of *Escherichia coli*, has been already cloned, and also determined for its nucleotide sequence (Fujita, N., Miwa, T., Ishijima, S., Izui, K. and Katsuki, H., *J. Biochem.*, 95, 909–916 (1984)). However, there is no report of a mutant in which inhibition by aspartic acid is desensitized.

The present invention has been made from the aforementioned viewpoint, an object of which is to provide a mutant phosphoenolpyruvate carboxylase with substantially desensitized feedback inhibition by aspartic acid, a gene conding for it, and a utilization method thereof.

DISCLOSURE OF THE INVENTION

As a result of diligent investigation in order to achieve the aforementioned object, the present inventors have found that the inhibition by aspartic acid is substantially desensitized by replacing an amino acid at a specified site of phosphoenolpyruvate carboxylase of *Escherichia coli* with another amino acid, succeeded in obtaining a gene coding for such a mutant enzyme, and arrived at completion of the present invention.

Namely, the present invention lies in a mutant phosphoenolpyruvate carboxylase, which originates from a microorganism belonging to the genus Escherichia, and has mutation to desensitize feedback inhibition by aspartic acid, and a DNA sequence coding for the mutant phosphoenolpyruvate carboxylase.

The present invention further provides microorganisms belonging to the genus Escherichia or coryneform bacteria harboring the DNA fragment, and a method of producing an amino acid wherein any of these microorganisms is cultivated in a preferable medium, and the amino acid selected from L-lysine, L-threonine, L-methionine, L-isoleucine, L-glutamic acid, L-arginine and L-proline is separated from the medium.

Incidentally, in this specification, the DNA sequence coding for the mutant phosphoenolpyruvate carboxylase, or a DNA sequence containing a promoter in addition thereto is occasionally merely referred to as "DNA sequence of the present invention", "mutant gene" or "phosphoenolpyruvate carboxylase gene."

The present invention will be explained in detail hereinafter.

<1> Mutant Phosphoenolpyruvate Carboxylase

The mutant phosphoenolpyruvate carboxylase of the present invention (hereinafter simply referred to as "mutant enzyme") lies in the phosphoenolpyruvate carboxylase of the microorganism belonging to the genus Escherichia, which has mutation to desensitize the feedback inhibition by aspartic acid.

Such mutation may be any one provided that the aforementioned feedback inhibition is substantially desensitized without losing the enzyme activity of the phosphoenolpyruvate carboxylase, for which there may be exemplified mutation which, when a mutant phosphoenolpyruvate carboxylase having the mutation is allowed to exist in cells of a microorganism belonging to the genus Escherichia, gives the cells resistance to a compound having the following properties:

it exhibits a growth inhibitory action against a microorganism belonging to the genus Escherichia which produces a wild type phosphoenolpyruvate carboxylase;

the aforementioned growth inhibitory action is recovered by existence of L-glutamic acid or L-aspartic acid; and it inhibits wild type phosphoenolpyruvic carboxylase activity.

More concretely, there may be exemplified, as counted from the N-terminus of the phosphoenolpyruvate carboxylase:

(1) mutation to replace 625th glutamic acid with lysine;
(2) mutation to replace 222th arginine with histidine and 223th glutamic acid with lysine, respectively;
(3) mutation to replace 288th serine with phenylalanine, 289th glutamic acid with lysine, 551th methionine with isoleucine and 804th glutamic acid with lysine, respectively;
(4) mutation to replace 867th alanine with threonine;

(5) mutation to replace 438th arginine with cysteine; and
(6) mutation to replace 620th lysine with serine.

Incidentally, as the phosphoenolpyruvate carboxylase of the microorganism belonging to the genus Escherichia, an amino acid sequence, which is deduced from a phosphoenolpyruvate carboxylase gene of *Escherichia coli* (Fujita, N., Miwa, T., Ishijima, S., Izui, K. and Katsuki, H., *J. Biochem.*, 95, 909–916 (1984)), is shown in SEQ ID NO:2 in the Sequence listing. In addition, an entire nucleotide sequence of a plasmid pT2, which contains the phosphoenolpyruvate carboxylase gene of *Escherichia coli*, is shown in SEQ ID NO:1 together with the amino acid sequence.

The aforementioned mutant enzymes are encoded by DNA sequences of the present invention described below, which are produced by expressing the DNA sequences in *Escherichia coli* and the like.

<2> DNA Sequence of the Present Invention and Microorganisms Harboring the Same

The DNA sequence of the present invention is DNA sequences coding for the aforementioned mutant enzymes, and has mutation to desensitize feedback inhibition of phosphoenolpyruvate carboxylase by aspartic acid in coding regions in DNA fragments coding for phosphoenolpyruvate carboxylase of the microorganism belonging to the genus Escherichia.

Concretely, there may be exemplified a DNA Sequence coding for the phosphoenolpyruvate carboxylase having the mutation of any one of the aforementioned (1) to (6), for example, with respect to the nucleotide sequence of SEQ ID NO:1, there may be exemplified a DNA sequence having any one of:

i) mutation to convert GAA of base Nos. 2109–2111 into AAA or AAG;
ii) mutation to convert CGC of base Nos. 900–902 into CAT or CAC, and GAA of 903–905 into AAA or AAG, respectively;
iii) mutation to convert TCT of base Nos. 1098–1100 into TTT or TTC, GAA of 1101–1103 into AAA or AAG, ATG of 1887–1889 into ATT, ATC or ATA, and GAA of 2646–2648 into AAA or AAG, respectively;
iv) mutation to convert GCG of 2835–2837 into any one of ACT, ACC, ACA and ACG; and
v) mutation to convert CGT of 1548–1550 into TGT or TGC; and
vi) mutation to convert AAA of 2094–2096 into TCT, TCC, TCA or TCG.

Such a mutant gene is obtained such that a recombinant DNA, which is obtained by ligating a phosphoenolpyruvate carboxylase gene as a wild type enzyme gene or having another mutation with a vector DNA adaptable to a host, is subjected to a mutation treatment, to perform screening from transformants by the recombinant DNA. Alternatively, it is also acceptable that a microorganism which produces a wild type enzyme is subjected to a mutation treatment, a mutant strain which produces a mutant enzyme is created, and then a mutant gene is screened from the mutant strain. For the mutation treatment of the recombinant DNA, hydroxylamine and the like may be used. Further, when an microorganism itself is subjected to a mutation treatment, a drug or a method usually used for artificial mutation may be used.

Further, in accordance with methods such as the Overlapping Extension method (Ho, S. N., Hunt, H. D., Horton, R. M., Pullen, J. K. and Pease, L. R., Gene, 77, 51–59 (1989)), the site specific mutation method (Kramer, W. and Frits, H. J., *Meth. in Enzymol.*, 154, 350 (1987); Kunkel, T. A. et al., *Meth. in Enzymol.*, 154, 367 (1987)) and the like, the aforementioned mutant gene can be also obtained by introducing mutation such as amino acid replacement, insertion, deletion and the like into a phosphoenolpyruvate carboxylase gene as a wild type enzyme gene or having another mutation. These methods are based on a principle that a non-mutated gene DNA is used as a template, and a synthetic DNA containing a mismatch at a mutation point is used as one of primers so as to synthesize complemental strands of the aforementioned gene DNA, thereby mutation is introduced. By using these methods, it is possible to cause intended mutation at an aimed site.

Alternatively, a sequence, which has restriction enzyme cleavage ends at both termini and includes both sides of a mutation point, is synthesized, and exchanged for a corresponding portion of a non-mutated gene, thereby mutation can be introduced (cassette mutation method).

The phosphoenolpyruvate carboxylase gene, which is the wild type enzyme gene or has another mutation to be used for introduction of mutation, may be any one provided that it is a gene coding for the phosphoenolpyruvate carboxylase of the microorganism belonging to the genus Escherichia, which is preferably determined for its base sequence and cloned. When it has not been cloned, a DNA fragment containing the gene can be amplified and isolated by using the PCR method and the like, followed by using a suitable vector to achieve cloning.

As the gene as described above, for example, there may be exemplified a gene of *Escherichia coli* having been cloned and determined for its base sequence (Fujita, N., Miwa, T., Ishijima, S., Izui, K. and Katsuki, H., *J. Biochem.*, 95, 909–916 (1984)). The sequence in the coding region of this gene is as shown in SEQ ID NO: 1 (base Nos. 237–2888).

Screening of a host harboring the mutant gene can be performed by using an analog compound of aspartic acid. The analog compound preferably has the following properties. Namely, it exhibits a growth inhibitory action against a microorganism belonging to the genus Escherichia which produces a wild type phosphoenolpyruvate carboxylase, the aforementioned growth inhibitory action is recovered by existence of L-glutamic acid or L-aspartic acid, and it inhibits wild type phosphoenolpyruvate carboxylase activity.

If a mutant strain beeing resistant to the analog compound mentioned above is selected from microorganism belonging to the genus Escherichia, for example, *Escherichia coli* HB101 producing wild type phosphoenolpyruvate carboxylase using inhibition of growth of the microorganism as an index, it is much likely to obtain a host microorganism which produces phosphoenolpyruvate carboxylase with desensitized feedback inhibition by aspartic acid.

It is proposed, as a general structure of an inhibitor of phosphoenolpyruvate carboxylase, that a C4 dicarboxylic acid structure is essentially provided. From such a viewpoint, various compounds were subjected to screening by the present inventors. *Escherichia coli* HB101 was cultivated in an LB medium, and transferred to M9 media (containing 20 μg/ml of thiamine and 3 μg/ml of each of Leu and Pro) containing any one of DL-2-amino-4-phosphonobutyric acid, bromosuccinic acid, meso-2,3-dibromosuccinic acid, 2,2-difluorosuccinic acid, 3-bromopyruvic acid, α-ketobutyric acid, α-ketoadipinic acid DL-threo-β-hydroxyaspartic acids L-aspartic acid β-metyl ester α-metyl-DL-aspartic acid, 2,3-diaminosuccinic acid or aspartic acid-β-hydrazide, and absorbance of the medium was measured at 660 nm with the passage of time, thereby growth was monitored.

Further, when these compounds were present at their growth inhibitory concentrations, it was investigated whether or not the inhibition was recovered by addition of nucleic acids (each of uridine, adenosine: 10 mg/dl), glutamic acid or amino acids of the aspartic acid family (Asp: 0.025%, each of Met, Thr, Lys: 0.1%).

As a result, three compounds: 3-bromopyruvate (3 BP) (1), aspartate-β-hydrazide (AHY) (2), and DL-threo-β-hydroxyaspartate (βHA) (3) were selected.

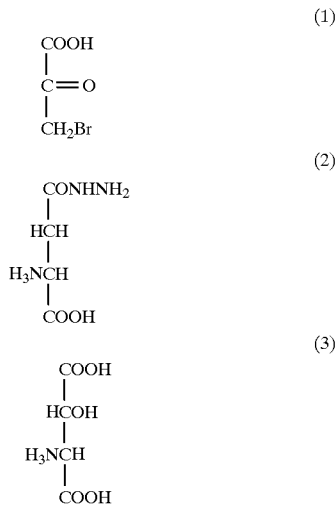

Growth inhibition of *Escherichia coli* by these analog compounds is shown in FIGS. 1–3. Further, growth recovery of *Escherichia coli*, in the case of addition of the aforementioned inhibition recovering substances alone or as a mixture of 2 species or 3 species, is shown in FIGS. 4–6. In addition, as a control, growth in the case of addition of the inhibition recovering substance in the absence of the inhibitory substance is shown in FIG. 7. Incidentally, in FIGS. 4–7, additives 1, 2 and 3 indicate nucleic acids, glutamic acid or amino acids of the aspartic acid family, respectively.

Further, inhibition of activity by the analog compound on phosphoenolpyruvate carboxylase was investigated. Crude enzyme was prepared from an *Escherichia coli* HB101 strain in accordance with a method described in *The Journal of Biochemistry*, Vol. 67, No. 4 (1970), and enzyme activity was measured in accordance with a method described in *Eur. J. Biochem.*, 202, 797–803 (1991).

*Escherichia coli* HB101 cultivated in an LB medium was disrupted, and a suspension was centrifuged to obtain a supernatant which was used as a crude enzyme solution. Measurement of enzyme activity was performed by measuring decrease in absorbance at 340 nm while allowing acetyl-coenzyme A known to affect the activity to exist at a concentration of 0.1 mM in a measurement system containing 2 mM potassium phosphoenolpyruvate, 0.1 mM NADH, 0.1M Tris-acetate (pH 8.5), 1.5 U malate dehydrogenase and crude enzyme. Results are shown in FIG. 8.

According to the results as above, it is apparent that the aforementioned three compounds inhibit growth of *Escherichia coli*, this inhibition cannot be recovered by nucleic acids alone, but the inhibition can be recovered by addition of glutamic acid or amino acids of the aspartic acid family. Therefore, these analog compounds were postulated to be selective inhibitors of phosphoenolpyruvate carboxylase. As shown in Examples described below, by using these compounds, the present invention has succeeded in selection of an *Escherichia coli* which produces the mutant phosphoenolpyruvate carboxylase.

When a transformant having an aimed mutant enzyme gene is screened by using the aforementioned compounds, and a recombinant DNA is recovered, then the mutant enzyme gene is obtained. Alternatively, in the case of a mutation treatment of an microorganism itself, when a mutant strain having an aimed mutant enzyme gene is screened by using the aforementioned compounds, a DNA fragment containing the aimed mutant enzyme gene is isolated from the strain, and it is ligated with a suitable vector, then the mutant enzyme gene is obtained.

On the other hand, as a result of diligent investigation by the present inventors taking notice of importance of an arginine residue in an aspartate binding protein of *Escherichia coli* (Krikos, A., Mouth, N., Boyd, A. and Simon, M. I. *Cell*, 33, 615–622 (1983), Mowbray, S. L and Koshland, D. E. *J. Biol. Chem.*, 264, 15638–15643 (1990), Milburn, M. V., Prive, G. G., Milligan, D. L., Scott, W. G., Yeh, J., Jancarik, J., Koshland, D. E. and Kim, S. H., *Science*, 254, 1342–1347 (1991)), it has been found that inhibition by aspartic acid is substantially desensitized by converting 438th arginine of phosphoenolpyruvate carboxylase into cysteine. In order to convert 438th arginine into cysteine, a codon of 438th arginine of a gene coding for phosphoenolpyruvate carboxylase may be converted into a codon of cysteine. For example, in SEQ ID NO:1, CGT of nucleotide numbers of 1548–1550 may be converted into TGT or TGC.

Further, the present inventors performed chemical modification of lysine residues of phosphoenolpyruvate carboxylase by using 2,4,6-trinitrobenzenesulfonic acid (TNBS) which is a compound to chemically modify lysine residues of a protein. During modification reaction, malic acid capable of serving as an inhibitor of phosphoenolpyruvate carboxylase was allowed to exist together. Namely, it was assumed that a lysine residue in the vicinity of a binding position of phosphoenolpyruvate carboxylase would be protected by bound malic acid and not be subjected to chemical modification. As a result, it was suggested that a 620th lysine residue was important for malic acid to bind phosphoenolpyruvate carboxylase, and it was found that the feedback inhibition by aspartic acid was desensitized while maintaining the enzyme activity of phosphoenolpyruvate carboxylase by converting the 620th lysine residue into a serine residue. In order to convert the 620th lysine residue into the serine residue, a codon of 620th lysine of the gene coding for phosphoenolpyruvate carboxylase may be converted into a codon of serine. For example, in SEQ ID NO:1, AAA having nucleotide numbers of 2094–2096 may be replaced with TCT, TCC, TCA, TCG, AGT or AGC.

In accordance with methods such as the Overlapping Extension method (Ho, S. N., Hunt, H. D., Horton, R. M., Pullen, J. K. and Pease, L. R., Gene, 77, 51–59 (1989)), the site specific mutation method (Kramer, W. and Frits, H. J., *Meth. in Enzymol.*, 154, 350 (1987); Kunkel, T. A. et al., *Meth. in Enzymol.*, 154, 367 (1987)) and the like, conversion of the codon can be also achieved by introducing mutation such as amino acid replacement, insertion, deletion and the like into a phosphoenolpyruvate carboxylase gene as a wild type enzyme gene or having another mutation. These methods are based on a principle that a non-mutated gene DNA is used as a template, and a synthetic DNA containing a mismatch at a mutation point is used as one of primers so as to synthesize complemental strands of the aforementioned gene DNA, thereby mutation is introduced. By using these methods, it is possible to cause intended mutation at an aimed site.

Alternatively, a sequence, which has restriction enzyme cleavage ends at both termini and contains both sides of a mutation point, is synthesized, and exchanged for a corresponding portion of a non-mutated gene, thereby mutation can be introduced (cassette mutation method).

The DNA fragment coding for the phosphoenolpyruvate carboxylase with mutation introduced as described above is expressed by using a suitable host-vector system, thereby it is possible to produce a mutant enzyme. Alternatively, even by performing transformation by integrating the DNA fragment of the present invention into a host chromosomal DNA, an aimed mutant enzyme can be produced.

As the host, there may be exemplified microorganisms belonging to the genus Escherichia, for example, *Escherichia coli*, coryneform bacteria and the like. The coryneform bacteria include bacteria belonging to the genus Corynebacterium, bacteria belonging to the genus Brevibacterium having been hitherto classified into the genus Brevibacterium but being united as bacteria belonging to the genus Corynebacterium at present, and bacteria belonging to the genus Brevibacterium closely related to bacteria belonging to the genus Corynebacterium. Incidentally, hosts which are preferable for amino acid production will be described below.

On the other hand, as the vector DNA, a plasmid vector is preferable, and those capable of self-replication in a host cell are preferable. When the host is *Escherichia coli*, for example, pUC19, pUC18, pBR322, pHSG299, pHSG399, RSF1010 and the like are exemplified. Alternatively, a vector of phage DNA can be also utilized.

Further, when the host is the coryneform bacteria, vectors which can be used and hosts which harbor them are exemplified below. Incidentally, deposition numbers of international depositories are shown in parentheses.

pAJ655 *Escherichia coli* AJ11882 (FERM BP-136)
  *Corynebacterium glutamicum* SR8201 (ATCC 39135)
pAJ1844 *Escherichia coli* AJ11883 (FERM BP-137)
  *Corvnebacterium glutamicum* SR8202 (ATCC 39136)
pAJ611 *Escherichia coli* AJ11884 (FERM BP-138)
pAJ3148 *Corynebacterium glutamicum* SR8203 (ATCC 39137)
pAJ440 *Bacillus subtilis* AJ11901 (FERM BP-140)

These vectors may be obtained from the deposited microorganisms as follows. Cells collected at the logarithmic growth phase are subjected to bacteriolysis by using lysozyme and SDS, and centrifuged at 30000×g to obtain a supernatant solution from a lysate, to which polyethylene glycol is added to perform separation and purification of the vectors by means of cesium chloride-ethidium bromide equilibrium density gradient centrifugation.

In order to transform *Escherichia coli* with a recombinant vector obtained by inserting the DNA sequence of the present invention into the aforementioned vector, it is possible to use a method usually used for transformation of *Escherichia coli*, such as a method in which cells are treated with calcium chloride to enhance permeability of DNA (Mandel, M. and Higa, A., *J. Mol. Biol.*, 53, 159 (1977)) and the like.

Further, as a method for transforming the coryneform bacteria, there is the aforementioned method in which cells are treated with calcium chloride, or a method in which incorporation is performed at a specified growth period in which cells can incorporate DNA (report in relation to *Bacillus subtilis* by Duncan, C. H. at al.). Further, incorporation into bacterial cells can be achieved by forming protoplasts or spheroplasts of DNA recipients which easily incorporate plasmid DNA. These are known for *Bacillus subtilis*, Actinomyces and yeast (Chang, S. et al., *Molec. Gen. Genet.*, 168, 111 (1979), Bibb et al., *Nature*, 274, 398 (1978), Hinnen, A. et al., *Proc. Natl. Acad. Sci. USA*, 75 1929 (1978)). Additionally, a method for transforming coryneform bacteria is disclosed in Japanese Patent Laid-open No. 2-207791.

In order to express the DNA sequence of the present invention in the aforementioned hosts, a promoter such as lac, trp, PL and the like which efficiently works in microorganisms may be used, or when the DNA sequence of the present invention contains a promoter of the phosphoenolpyruvate carboxylase gene, it may be used as it is. Alternatively, when the coryneform bacterium is used as the host, it is also possible to use a known trp promoter originating from a bacterium belonging to the genus Brevibacterium (Japanese Patent Laid-open No. 62-244382) and the like.

Further, as described above, it is acceptable that the DNA sequence of the present invention is inserted into the vector DNA capable of self-replication and introduced into the host to allow the host to harbor it as a plasmid, and it is also acceptable that the DNA sequence of the present invention is integrated into a chromosome of an microorganism by means of a method using transposon (Berg, D. E. and Berg, C. M., *Bio/Technol.*, 1, 417 (1983)), Mu phage (Japanese Patent Laid-open No. 2-109985) or homologous recombination (*Experiments in Molecular Genetics*, Cold Spring Harbor Lab. (1972)). In addition, in order to integrate the DNA of the present invention into the coryneform bacteria, it is possible to utilize a temperature-sensitive plasmid disclosed in Japanese Patent Laid-open No. 5-7491.

When the microorganism transformed with the DNA sequence of the present invention as described above is cultivated, and this DNA sequence is expressed, then a mutant enzyme is obtained. It becomes apparent, by measuring the activity by adding aspartic acid to an enzyme reaction system, whether or not the mutant enzyme thus obtained has desensitized feedback inhibition by aspartic acid. It is possible for the measurement of the enzyme activity to use a spectrometric method (Yoshinage, T., Izui, K. and Katsuki, H., *J. Biochem.*, 68, 747–750 (1970)) and the like.

Further, the DNA sequence of the present invention codes for the mutant enzyme in which feedback inhibition by aspartic acid is desensitized, so that the microorganism harboring this DNA sequence can be utilized for efficient fermentative production of amino acids of the aspartic acid family and the glutamic acid family as described below.

*Escherichia coli* AJ12907, AJ12908, AJ12909 and AJ12910 harboring the mutant enzyme genes obtained in Examples described below are deposited in National Institute of Bioscience and Human Technology of Agency of Industrial Science and Technology (1-3, Higashi 1-chome, Tsukuba-shi, Ibaraki-ken, Japan; zip code 305) on Aug. 3, 1993 under the deposition numbers of FERM P-13774, FERM P-13775, FERM P-13776 and FERM P-13777, transferred from the original deposition to international deposition based on Budapest Treaty on Jul. 11, 1994 and has been deposited as deposition numbers of FERM BP-4734, FERM BP-4735, FERM BP-4736, FERM BP-4737, respectively in this order.

<3> Production Method of Amino Acids

Amino acids can be produced by cultivating the microorganism harboring the DNA sequence of the present invention in a preferable medium, and separating generated amino acids. As such amino acids, there may be exemplified L-lysine, L-threonine, L-methionine, L-isoleucine, L-glutamic acid, L-arginine and L-proline.

Preferable hosts into which the DNA sequence of the present invention is introduced to be used for production of each of the amino acids, and a cultivation method will be exemplified below.

(1) Hosts Preferable for the Amino Acid Production Method of the Present Invention (i) Hosts preferable for L-lysine production As the host to be used for L-lysine production according to the present invention, there may be exemplified bacteria belonging to the genus Escherichia, preferably L-lysine-producing *Escherichia coli*. Concretely, a mutant strain having resistance to a lysine analog can be exemplified. Such a lysine analog is those which inhibit growth of microorganisms belonging to the genus Escherichia, however, the suppression is totally or partially desensitized provided that L-lysine co-exits in the medium. For example, there are oxalysine, lysine hydroxamate, S-(2-aminoethyl)-cysteine (hereinafter abbreviated as "AEC"), γ-methyllysine, α-chlorocaprolactam and the like. Mutant strains having resistance to these lysine analogs can be obtained by applying an ordinary artificial mutation treatment to microorganisms belonging to the genus Escherichia. Concretely, as a bacterial strain to be used for L-lysine production, there may be exemplified *Escherichia coli* AJ11442 (deposited as FERM P-5084, see lower-left column on page 471 in Japanese Patent Laid-open No. 56-18596).

On the other hand, various artificial mutant strains of coryneform bacteria which have been used as L-lysine-producing bacteria can be used for the present invention. Such artificial mutant strains are as follows: AEC resistant mutant strain; mutant strain which requires amino acid such as L-homoserine for its growth (Japanese Patent Publication Nos. 48-28078 and 56-6499); mutant strain which exhibits resistance to AEC and requires amino acid such as L-leucine, L-homoserine, L-proline, L-serine, L-arginine, L-alanine, L-valine and the like (U.S. Pat. Nos. 3,708,395 and 3,825,472); L-lysine-producing mutant strain which exhibits resistance to DL-α-amino-ε-caprolactam, α-amino-lauryllactam, quinoid and N-lauroylleucine; L-lysine-producing mutant strain which exhibits resistance to an inhibitor of oxaloacetate decarboxylase or respiratory system enzyme (Japanese Patent Laid-open Nos. 50-53588, 50-31093, 52-102498, 53-86089, 55-9783, 55-9759, 56-32995 and 56-39778, and Japanese Patent Publication Nos. 53-43591 and 53-1833); L-lysine-producing mutant strain which requires inositol or acetic acid (Japanese Patent Laid-open Nos. 55-9784 and 56-8692); L-lysine-producing mutant strain which exhibits sensitivity to fluoropyruvate or temperature not less than 34° C. (Japanese Patent Laid-open Nos. 55-9783 and 53-86090); and mutant strain of Brevibacterium or Corynebacterium which exhibits resistance to ethylene glycol and produces L-lysine (see U.S. patent application Ser. No. 333455).

Followings are exemplified as concrete coryneform bacteria to be used for lysine production:

*Brevibacterium lactofermentum* AJ12031 (FERM-BP277), see page 525 in Japanese Patent Laid-open No. 60-62994;

*Brevibacterium lactofermentum* ATCC 39134, see lower-right column on page 473 in Japanese Patent Laid-open No. 60-62994;

*Brevibacterium lactofermentum* AJ3463 (FERM-P1987), see Japanese Patent Publication No. 51-34477.

In addition, wild strains of coryneform bacteria described below can be also used for the present invention in the same manner.

| | |
|---|---|
| *Corynebacterium acetoacidophilum* | ATCC 13870 |
| *Corynebacterium acetoglutamicum* | ATCC 15806 |
| *Corynebacterium callunae* | ATCC 15991 |
| *Corynebacterium glutamicum* | ATCC 13032 |
| | ATCC 13060 |
| (*Brevibacterium divaricatum*) | ATCC 14020 |
| (*Brevibacterium lactofermentum*) | ATCC 13869 |
| (*Corynebacterium lilium*) | ATCC 15990 |
| *Corynebacterium melassecola* | ATCC 17965 |
| *Brevibacterium saccharolyticum* | ATCC 14066 |
| *Brevibacterium immariophilum* | ATCC 14068 |
| *Brevibacterium roseum* | ATCC 13825 |
| *Brevibacterium flavum* | ATCC 13826 |
| *Brevibacterium thiogenitalis* | ATCC 19240 |
| *Microbacterium ammoniaphilum* | ATCC 15354 |

(ii) Hosts preferable for L-threonine production

*Escherichia coli* B-3996 (RIA 1867), see Japanese Patent Laid-open No. 3-501682 (PCT);

*Escherichia coli* AJ12349 (FERM-P9574), see upper-left column on page 887 in Japanese Patent Laid-open No. 2-458;

*Escherichia coli* AJ12351 (FERM-P9576), see lower-right column on page 887 in Japanese Patent Laid-open No. 2-458;

*Escherichia coli* AJ12352 (FERM P-9577), see upper-left column on page 888 in Japanese Patent Laid-open No. 2-458;

*Escherichia coli* AJ11332 (FERM P-4898), see upper-left column on page 889 in Japanese Patent Laid-open No. 2-458;

*Escherichia coli* AJ12350 (FERM P-9575), see upper-left column on page 889 in Japanese Patent Laid-open No. 2-458;

*Escherichia coli* AJ12353 (FERM P-9578), see upper-right column on page 889 in Japanese Patent Laid-open No. 2-458;

*Escherichia coli* AJ12358 (FERM P-9764), see upper-left column on page 890 in Japanese Patent Laid-open No. 2-458;

*Escherichia coli* AJ12359 (FERM P-9765), see upper-left column on page 890 in Japanese Patent Laid-open No. 2-458;

*Escherichia coli* AJ11334 (FERM P-4900), see column 6 on page 201 in Japanese Patent Publication No. 1-29559;

*Escherichia coli* AJ11333 (FERM P-4899), see column 6 on page 201 in Japanese Patent Publication No. 1-29559;

*Escherichia coli* AJ11335 (FERM P-4901), see column 7 on page 202 in Japanese Patent Publication No. 1-29559.

Following bacterial strains are exemplified as the coryneform bacteria:

*Brevibacterium lactofermentum* AJ11188 (FERM P4190), see upper-right column on page 473 in Japanese Patent Laid-open No. 60-87788;

*Corynebacterium plutamicum* AJ11682 (FERM BP-118), see column 8 on page 230 in Japanese Patent Publication No. 2-31956;

*Brevibacterium flavum* AJ11683 (FERM BP-119), see column 10 on page 231 in Japanese Patent Publication No. 2-31956.

(iii) Hosts preferable for L-methionine production

Following bacterial strains are exemplified for L-methionine production:

*Escherichia coli* AJ11457 (FERM P-5175), see upper-right column on page 552 in Japanese Patent Laid-open No. 56-35992;

*Escherichia coli* AJ11458 (FERM P-5176), see upper-right column on page 552 in Japanese Patent Laid-open No. 56-35992;

*Escherichia coli* AJ11459 (FERM P-5177), see upper-right column on page 552 in Japanese Patent Laid-open No. 56-35992;

*Escherichia coli* AJ11539 (FERM P-5479), see lower-left column on page 435 in Japanese Patent Laid-open No. 56-144092;

*Escherichia coli* AJ11540 (FERM P-5480), see lower-left column on page 435 in Japanese Patent Laid-open No. 56-144092;

*Escherichia coli* AJ11541 (FERM P-5481), see lower-left column on page 435 in Japanese Patent Laid-open No. 56-144092;

*Escherichia coli* AJ11542 (FERM P-5482), see lower-left column on page 435 in Japanese Patent Laid-open No. 56-144092.

(iv) Hosts preferable for L-aspartic acid production

Following bacterial strains are exemplified for L-aspartic acid production:

*Brevibacterium flavum* AJ3859 (FERM P-2799), see upper-left column on page 524 in Japanese Patent Laid-open No. 51-61689;

*Brevibacterium lactofermentum* AJ3860 (FERM P-2800), see upper-left column on page 524 in Japanese Patent Laid-open No. 51-61689;

*Corynebacterium acetoacidophilum* AJ3877 (FERM-P2803), see upper-left column on page 524 in Japanese Patent Laid-open No. 51-61689;

*Corynebacterium glutamicum* AJ3876 (FERM P-2802), see upper-left column on page 524 in Japanese Patent Laid-open No. 51-61689.

(v) Hosts preferable for L-isoleucine production

*Escherichia coli* KX141 (VKPM-B4781) (see 45th paragraph in Japanese Patent Laid-open No. 4-33027) is exemplified as the bacteria belonging to the genus Escherichia, and *Brevibacterium lactofermentum* AJ12404 (FERM P-10141) (see lower-left column on page 603 in Japanese Patent Laid-open No. 2-42988) and *Brevibacterium flavum* AJ12405 (FERM P-10142) (see lower-left column on page 524 in Japanese Patent Laid-open No. 2-42988) are exemplified as the coryneform bacteria.

(vi) Hosts preferable for L-glutamic acid production

Following bacterial strains are exemplified as the bacteria belonging to the genus Escherichia:

*Escherichia coli* AJ12628 (FERM P-12380), see French Patent Publication No. 2 680 178 (1993);

*Escherichia coli* AJ12624 (FERM P-12379), see French Patent Publication No. 2 680 178 (1993).

Following bacterial strains are exemplified as the coryneform bacteria:

*Brevibacterium lactofermentum* AJ12745 (FERM BP-2922), see lower-right column on page 561 in Japanese Patent Laid-open No. 3-49690;

*Brevibacterium lactofermentum* AJ12746 (FERM BP-2923), see upper-left column on page 562 in Japanese Patent Laid-open No. 3-49690;

*Brevibacterium lactofermentum* AJ12747 (FERM BP-2924), see upper-left column on page 562 in Japanese Patent Laid-open No. 3-49690;

*Brevibacterium lactofermentum* AJ12748 (FERM BP-2925), see upper-left column on page 562 in Japanese Patent Laid-open No. 3-49690;

*Brevibacterium flavum* ATCC 14067, see Table 1 on page 3 in Japanese Patent Laid-open No. 5-3793;

*Corynebacterium glutamicum* ATCC 21492, see Table 1 on page 3 in Japanese Patent Laid-open No. 5-3793.

(vii) Hosts preferable for L-arginine production

Following bacterial strains are exemplified as the bacteria belonging to the genus Escherichia:

*Escherichia coli* AJ11593 (FERM P-5616), see upper-left column on page 468 in Japanese Patent Laid-open No. 57-5693;

*Escherichia coli* AJ11594 (FERM P-5617), see upper-right column on page 468 in Japanese Patent Laid-open No. 57-5693.

Following bacterial strains are exemplified as the coryneform bacteria:

*Brevibacterium flavum* AJ12144 (FERM P-7642), see column 4 on page 174 in Japanese Patent Publication No. 5-27388:

*Corynebacterium glutamicum* AJ12145 (FERM P-7643), see column 4 on page 174 in Japanese Patent Publication No. 5-27388;

*Brevibacterium flavum* ATCC 21493, see Table 1 on page 3 in Japanese Patent Laid-open No. 5-3793;

*Corynebacterium glutamicum* ATCC 21659, see Table 1 on page 3 in Japanese Patent Laid-open No. 5-3793.

(viii) Hosts preferable for L-proline production

Following bacterial strains are exemplified as the bacteria belonging to the genus Escherichia:

*Escherichia coli* AJ11543 (FERM P-5483), see lower-left column on page 435 in Japanese Patent Laid-open No. 56-144093;

*Escherichia coli* AJ11544 (FERM P-5484), see lower-left column on page 435 in Japanese Patent Laid-open No. 56-144093.

Following bacterial strains are exemplified as the coryneform bacteria:

*Brevibacterium lactofermentum* AJ11225 (FERM P-4370), see upper-left column on page 473 in Japanese Patent Laid-open No. 60-87788;

*Brevibacterium flavum* AJ11512 (FERM P-5332), see column 2 on page 185 in Japanese Patent Publication No. 62-36679;

*Brevibacterium flavum* AJ11513 (FERM P-5333), see column 2 on page 185 in Japanese Patent Publication No. 62-36679;

*Brevibacterium flavum* AJ11514 (FERM P-5334), see column 2 on page 185 in Japanese Patent Publication No. 62-36679;

*Corynebacterium glutamicum* AJ11522 (FERM P-5342), see column 2 on page 185 in Japanese Patent Publication No. 62-36679;

*Corynebacterium glutamicum* AJ11523 (FERM P-5343), see column 2 on page 185 in Japanese Patent Publication No. 62-36679.

(2) Cultivation Method

The method for cultivating the aforementioned hosts is not especially different from a cultivation method for amino acid-producing microorganisms in the prior art. Namely, an ordinary medium is used containing a carbon source, a nitrogen source and inorganic ions, and optionally organic trace nutrients such as amino acids, vitamins and the like.

As the carbon source, glucose, sucrose, lactose and the like, as well as starch hydrolysate, whey, molasses and the like containing them may be used. As the nitrogen source, ammonia gas, aqueous ammonium, ammonium salt and the like can be used. Incidentally, when a nutrient requiring mutant strain for amino acids or the like is used as the host, it is necessary to suitably add the nutrient such as amino acid or the like required by the strain to the medium. An example of the medium for lysine production is shown in Table 1 below as a medium to be used for amino acid production. Incidentally, calcium carbonate is added to other components after being separately sterilized.

TABLE 1

| Medium component | Blending amount |
| --- | --- |
| glucose | 5 g/dl |
| $(NH_4)_2SO_4$ | 2.5 g/dl |
| $KH_2PO_4$ | 0.2 g/dl |
| $MgSO_4 \cdot 7H_2O$ | 0.1 g/dl |
| yeast extract | 0.05 g/dl |
| thiamine hydrochloride | 1 µg/l |
| biotin | 300 µg/l |
| $FeSO_4 \cdot 7H_2O$ | 1 mg/dl |
| $MnSO_4 \cdot 4H_2O$ | 1 mg/dl |
| calcium carbonate | 2.5 g/dl |
| (pH 7.0) | |

The cultivation is performed until generation and accumulation of amino acids substantially stop while suitably controlling pH and temperature of the medium under an aerobic condition. In order to collect amino acids thus accumulated in the cultivated medium, an ordinary method can be applied.

BEST MODE FOR CARRYING OUT THE INVENTION

Figure 1:
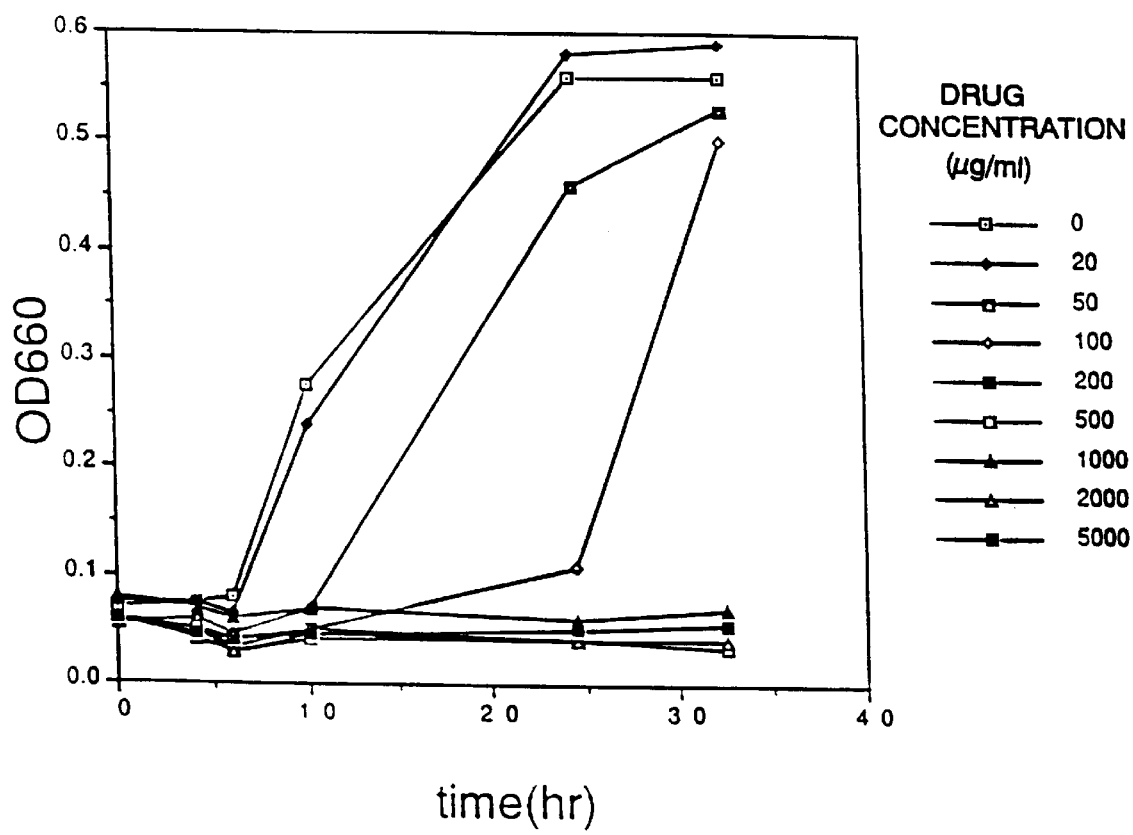
FIG. 1 shows growth inhibition by 3-bromopyruvate.
Figure 2:
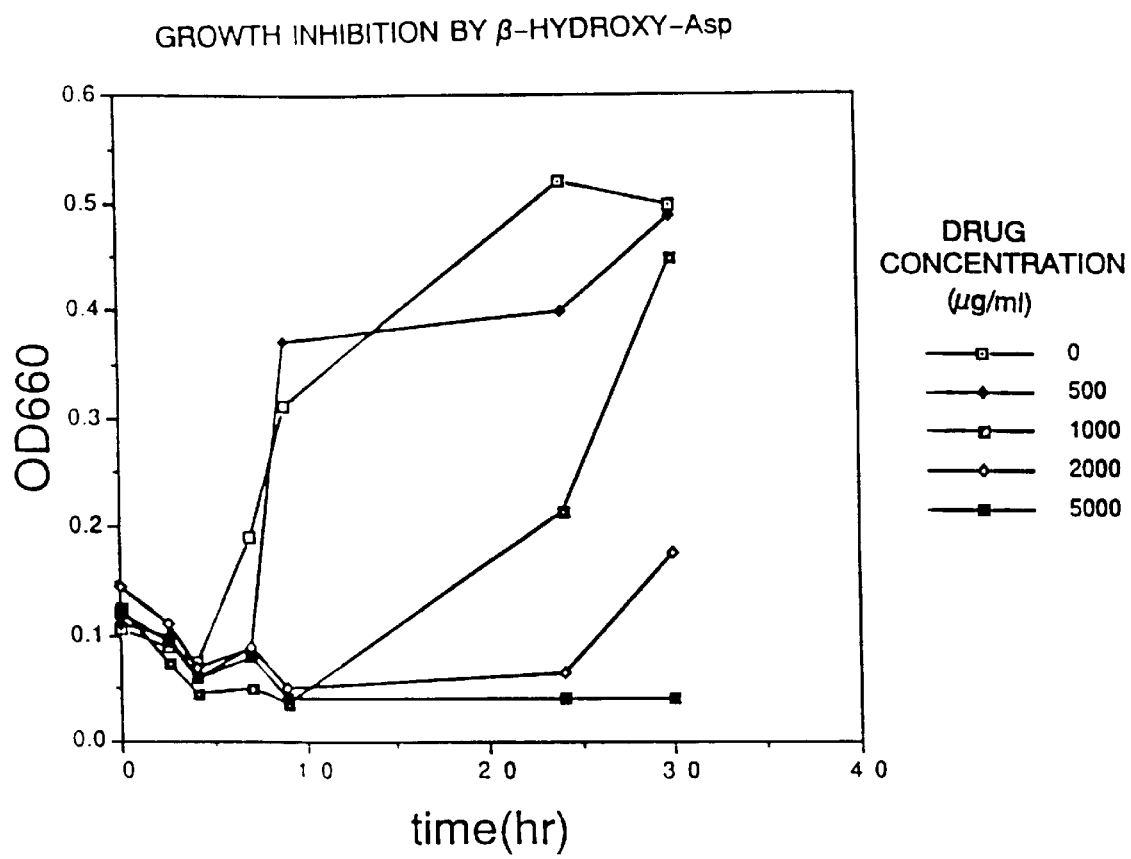
FIG. 2 shows growth inhibition by aspartate-β-hydrazide.
Figure 3:
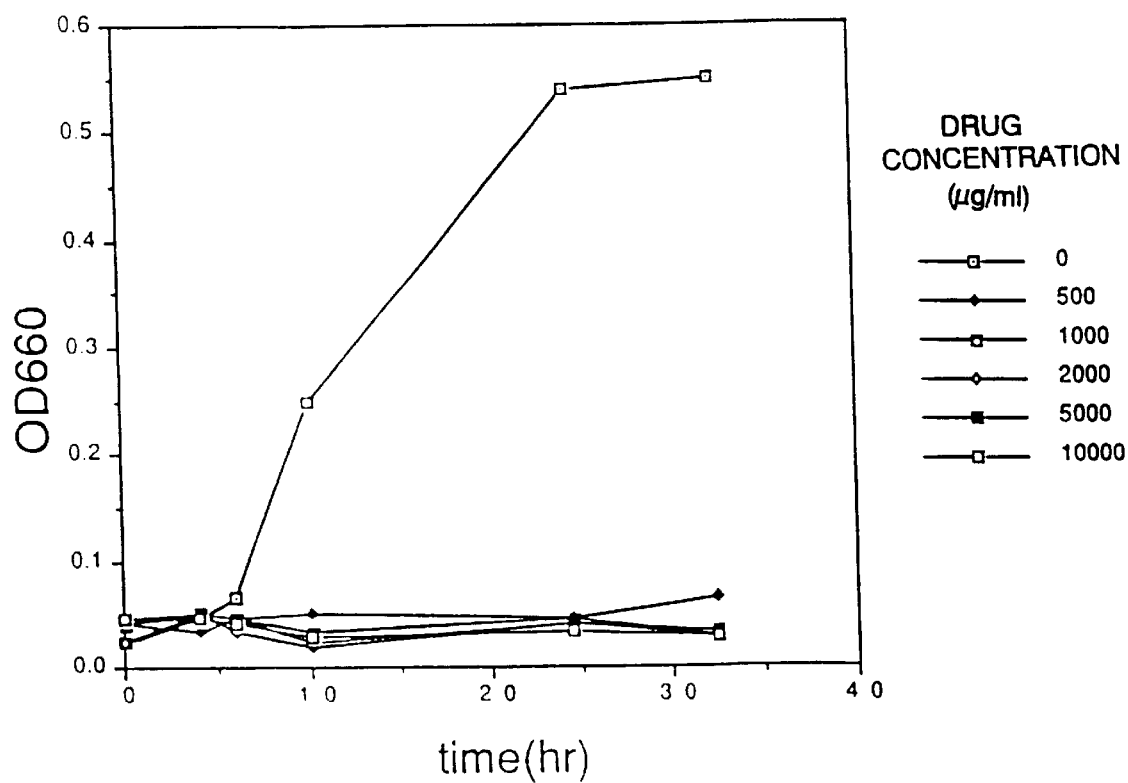
FIG. 3 shows growth inhibition by DL-threo-β-hydroxyaspartate.
Figure 4:
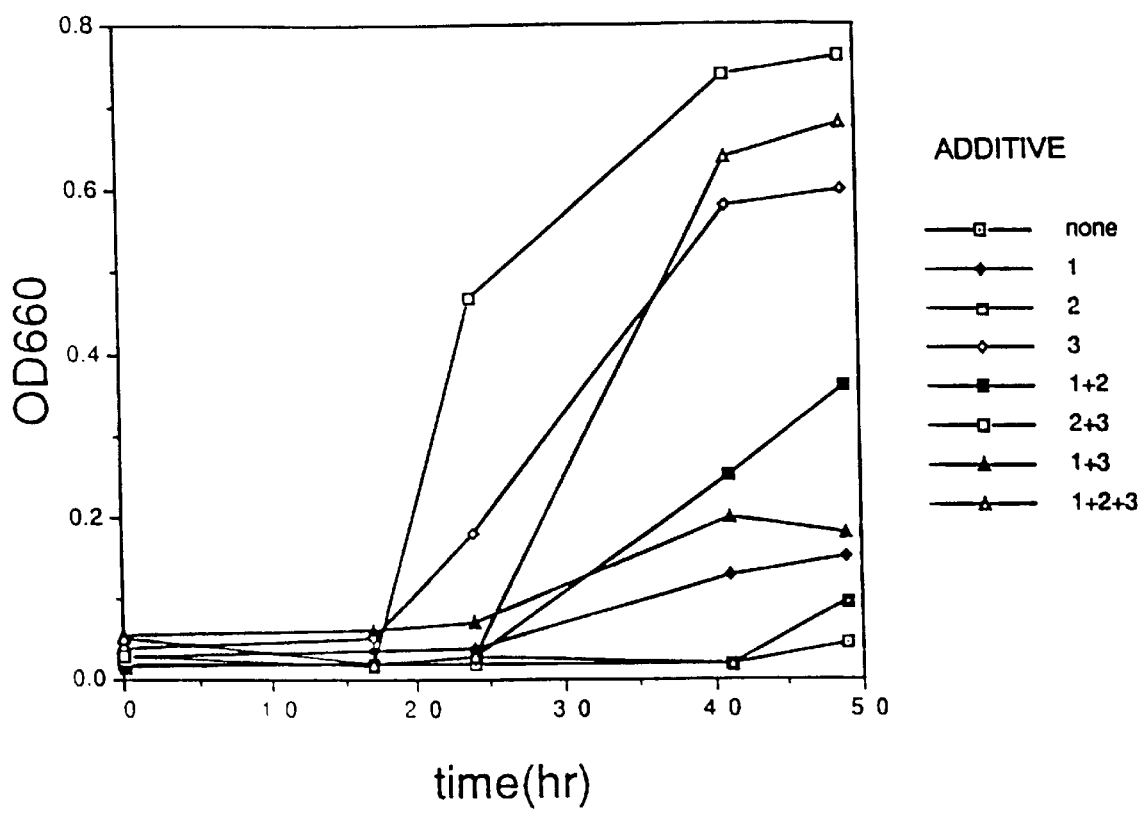
FIG. 4 shows effects of inhibition recovering substances on 3-bromopyruvate.
Figure 5:
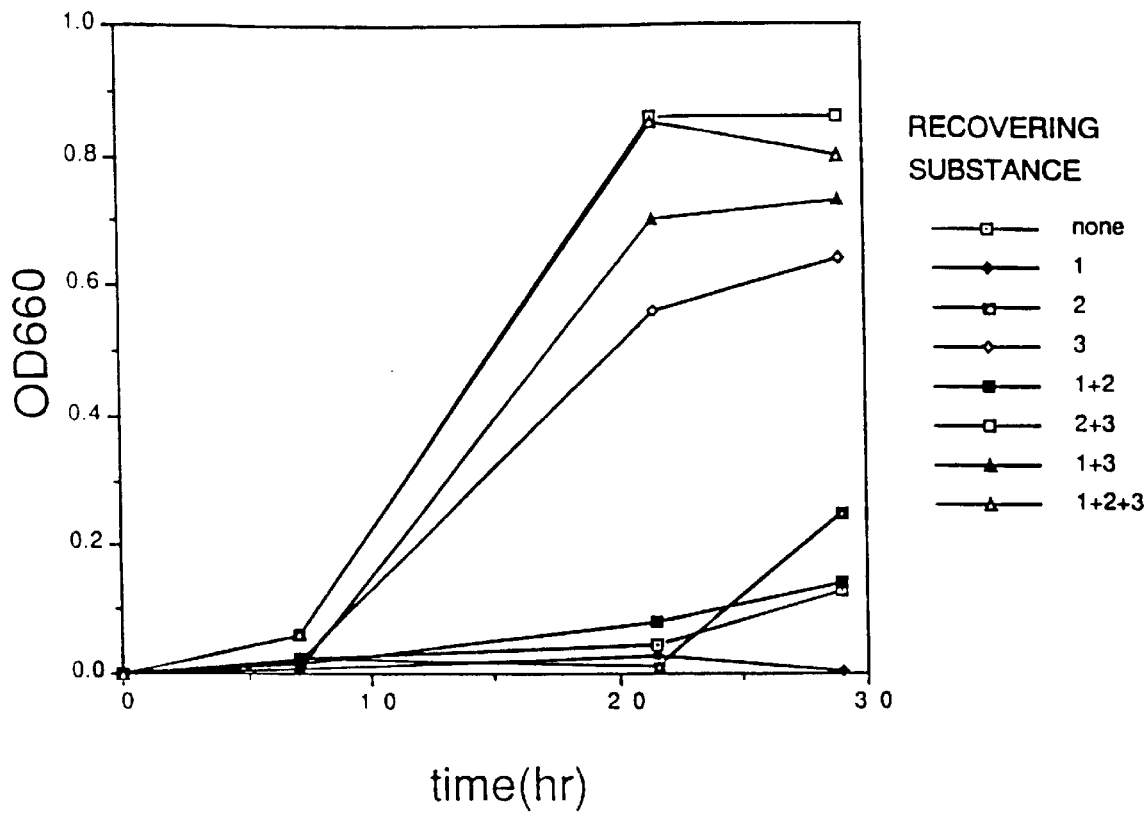
FIG. 5 shows effects of inhibition recovering substances on aspartate-β-hydrazide.
Figure 6:
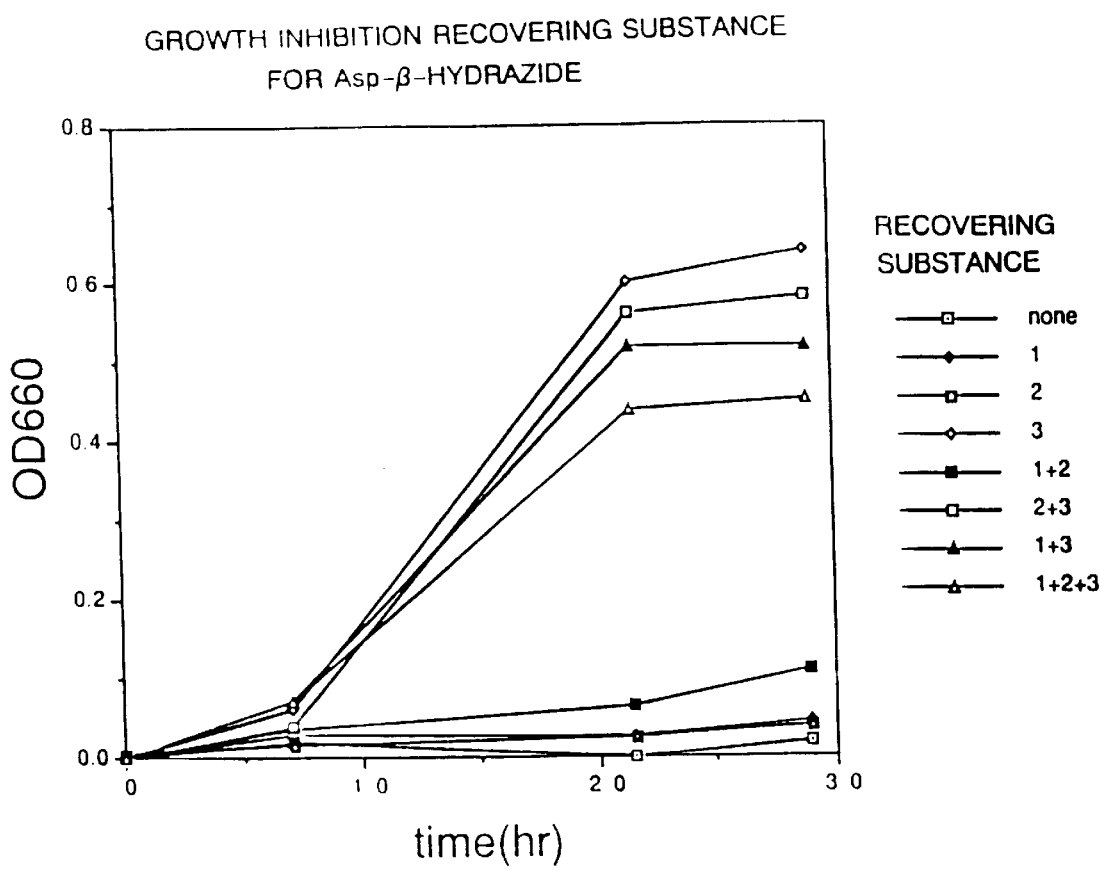
FIG. 6 shows effects of inhibition recovering substances on DL-threo-β-hydroxyaspartate.
Figure 7:
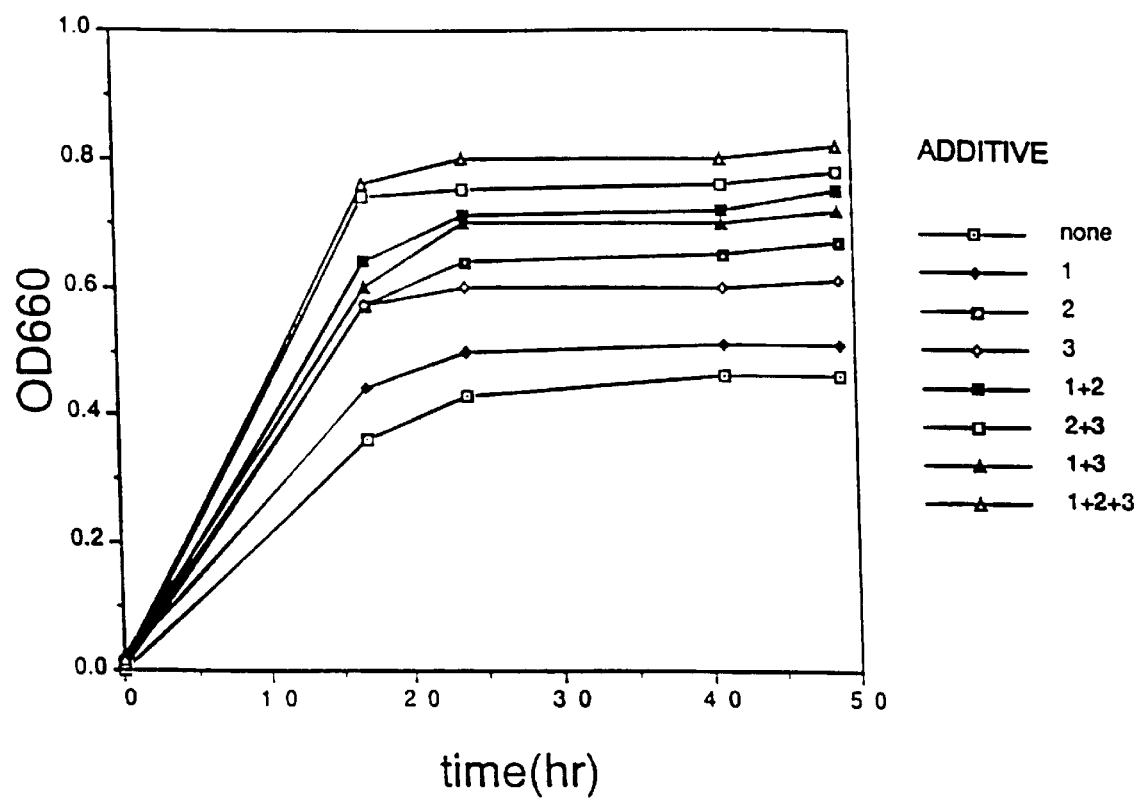
FIG. 7 shows influences exerted on growth by growth recovering factors.
Figure 8:
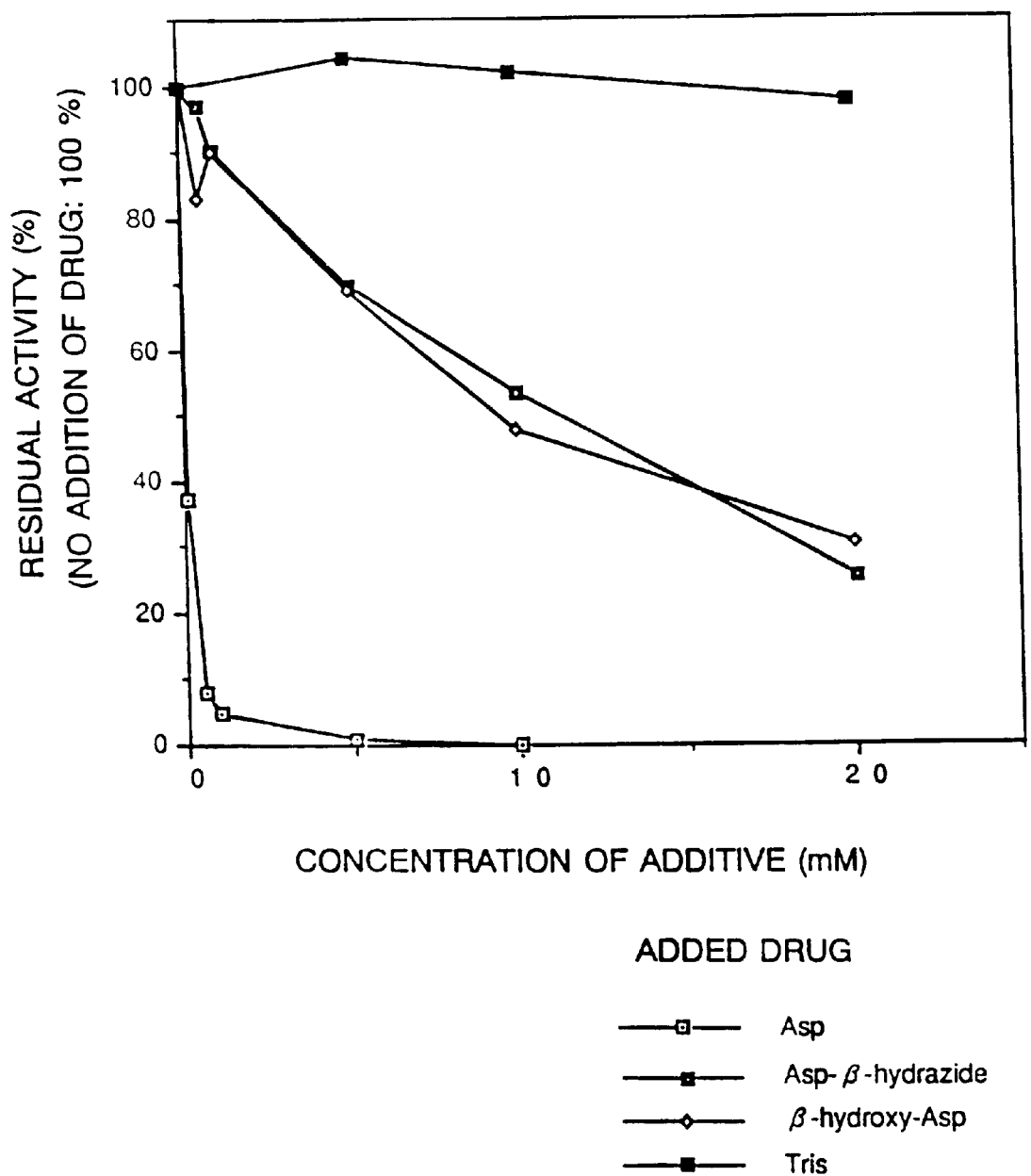
FIG. 8 shows inhibition of phosphoenolpyruvate carboxylase by growth inhibitory substances.

The present invention will be explained more concretely below with reference to Examples.

EXAMPLE 1

Acquisition of Mutant Phosphoenolpyruvate Carboxylase Gene

A mutant gene was prepared by using a plasmid pS2 obtained by inserting a phosphoenolpyruvate carboxylase gene having been cloned and determined for its base sequence into a SalI site of a vector plasmid pBR322. pS2 has an ampicillin resistance gene as a drug resistance marker gene (Sabe, H. et al., *Gene*, 31, 279–283 (1984)). The nucleotide sequence of the phosphoenolpyruvate carboxylase gene contained in pS2 is the same as that contained in the aforementioned plasmid pT2.

pS2 DNA was treated at 75° C. for 2 hours with a hydroxylamine treating solution (20 µg/ml pS2 DNA, 0.05M sodium phosphate (pH 6.0), 1 mM EDTA, 0.4M hydroxylamine). Because of influence by pH on the hydroxylamine treatment, 80 µl of 1M hxydroxylamine.HCl and 1 mM EDTA solution having a pH adjusted to 6.0 with sodium hydroxide, 100 µl of 0.1M sodium phosphate (pH 6.0) and 1 mM EDTA solution, and TE (10 mM Tris-HCl, 1 mM EDTA) buffer containing 2 µg of pS2 DNA were mixed, to finally provide 200 µl with water.

The aforementioned condition is a condition in which transformants has a survival ratio of 0.2% based on a state before the treatment in an ampicillin-containing medium when *Escherichia coli* HB101 is transformed with pS2 after the treatment.

*Escherichia coli* HB101 was transformed with pS2 treated with hydroxylamine, which was spread on a solid plate medium containing ampicillin to obtain about 10000 colonies of transformants. They were suspended in a liquid medium, and spread on a solid plate medium containing any one of 3-bromopyruvate (3BP), aspartate-β-hydroxamate (AHX), aspartate-β-hydrazide (AHY) and DL-threo-β-hydroxyaspartate (β HA) as the analog compounds of aspartic acid at a concentration near a minimal inhibitory concentration to give $10^3$ to $10^5$ cells per one medium plate, and growing colonies were selected.

From 100 strains of analog compound resistant strains thus obtained, phosphoenolpyruvate carboxylase produced by each of them was partially purified in accordance with a method described in *The Journal of Biochemistry*, Vol. 67, No. 4 (1970), and inhibition of enzyme activity by the analog compounds was investigated. Measurement of the enzyme activity was performed in the same manner as described above.

Further, plasmids were isolated from bacterial strains producing mutant enzymes with activities not inhibited by the analog compounds, and were introduced into *Escherichia coli* PCR1 as a phosphoenolpyruvate carboxylase deficient strain (Sabe, H. et al., *Gene*, 31, 279–283 (1984)), to confirm production of the mutant enzymes.

Five transformants harboring mutant enzyme genes were thus obtained. As a result of determination of base sequences of these genes, 2 strains had the same mutation, and 4 kinds of mutant genes were obtained. The transformants harboring them were designated as AJ12907, AJ12908, AJ12909 and AJ12910, and were deposited in National Institute of Bioscience and Human Technology of Agency of Industrial Science and Technology1-3, Higashi 1-chome, Tsukuba-shi, Ibaraki-ken, Japan; zip code 305) on Aug. 3, 1993 under the deposition numbers of FERM P-13774, FERM P-13775, FERM P-13776 and FERM P-13777, transferred from the original deposition to international deposition based on Budapest Treaty on Jul. 11, 1994 and has been deposited as deposition numbers of FERM BP-4734, FERM BP-4735, FERM BP-4736, FERM BP-4737, respectively in this order. Further, the plasmids possessed by them were designated as pBP5, pHA19, pBP122 and pR6 respectively in this order. Mutations possessed by the phosphoenolpyruvate carboxylase genes contained in each of the plasmids are shown in Table 2. Numerical values in the table indicate nucleotide numbers or amino acid numbers in SEQ ID NO:1.

TABLE 2

| Transformant | Plasmid | Mutation | Amino acid replacement associated with mutation |
|---|---|---|---|
| AJ12907 | pBP5 | $^{2109}G \rightarrow A$ | $^{625}Glu \rightarrow Lys$ |
| AJ12908 | pHA19 | $^{901}G \rightarrow A$ | $^{222}Arg \rightarrow His$ |
|  |  | $^{903}G \rightarrow A$ | $^{223}Glu \rightarrow Lys$ |
| AJ12909 | pBP122 | $^{1099}C \rightarrow T$ | $^{288}Ser \rightarrow Phe$ |
|  |  | $^{1101}G \rightarrow A$ | $^{289}Glu \rightarrow Lys$ |
|  |  | $^{1889}G \rightarrow A$ | $^{551}Met \rightarrow Ile$ |
|  |  | $^{2646}G \rightarrow A$ | $^{804}Glu \rightarrow Lys$ |
| AJ12910 | pR6 | $^{2835}G \rightarrow A$ | $^{867}Ala \rightarrow Thr$ |

Incidentally, selection was performed for AJ12907 and AJ12909 in a medium containing 500 µg/ml of 3BP, for AJ12908 in a medium containing 1000 µg/ml of βHA, and for AJ12910 in a medium containing 500 µg/ml of AHY.

EXAMPLE 2

Mutant Phosphoenolpyruvate Carboxylase

Sensitivity to aspartic acid was investigated for phosphoenolpyruvate carboxylases produced by the aforementioned 4 transformants. These bacterial strains are deficient in the phosphoenolpyruvate carboxylase gene originating from the host, so that produced phosphoenolpyruvate carboxylase originates from the plasmid.

Figure 9:
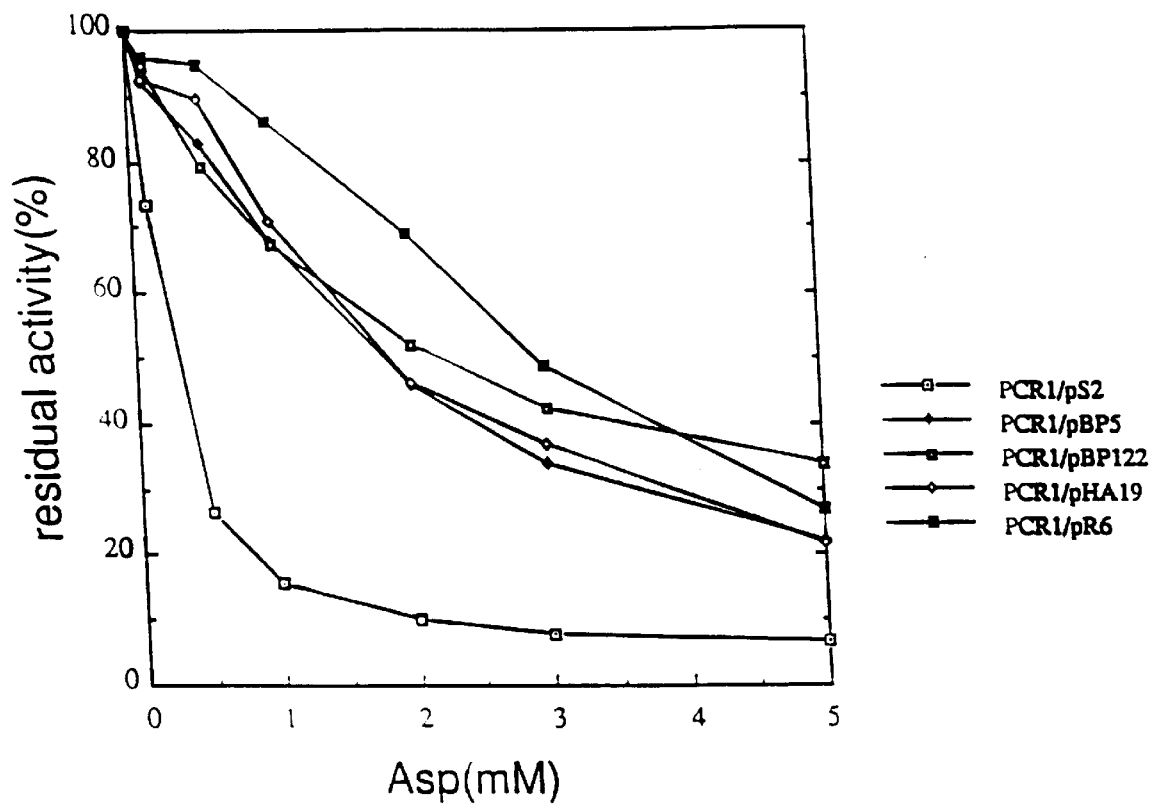
FIG. 9 shows inhibition of phosphoenolpyruvate carboxylase of the present invention by aspartic acid.
Figure 10:
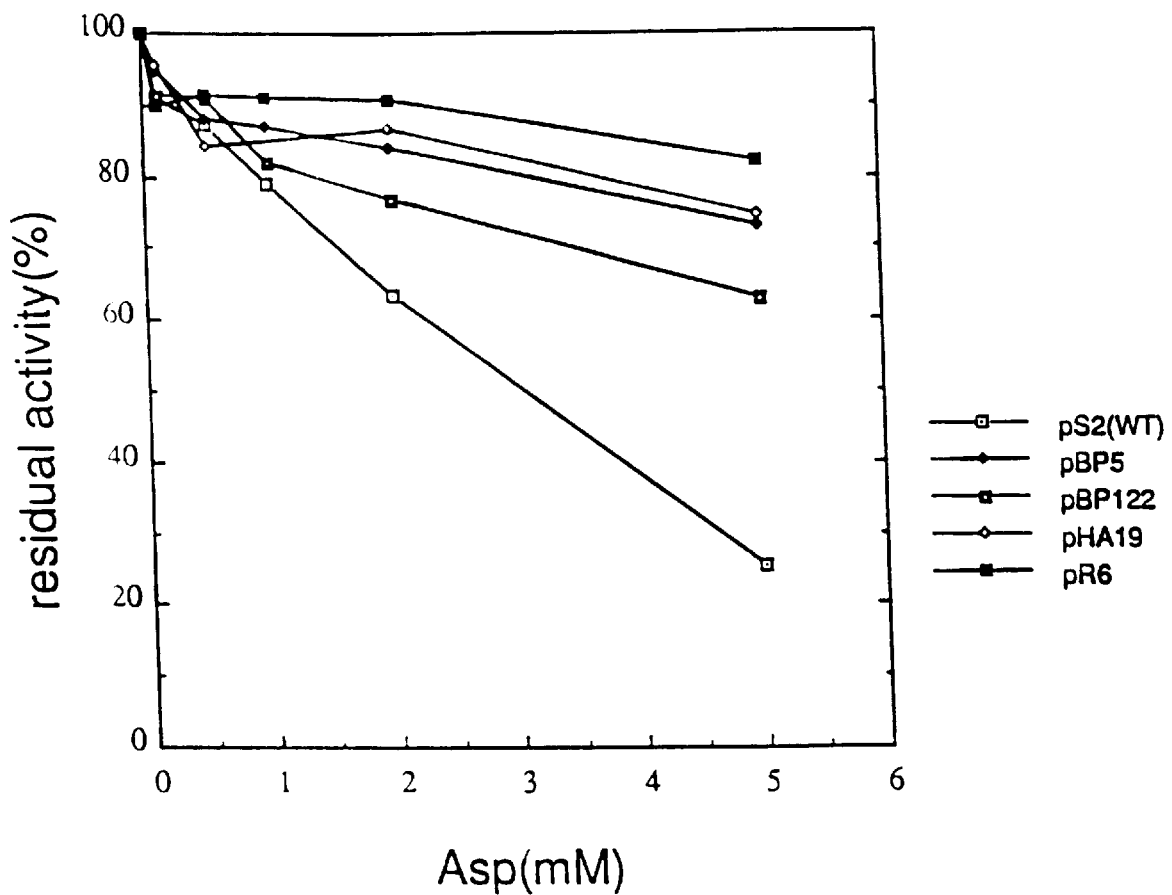
FIG. 10 shows inhibition of phosphoenolpyruvate carboxylase of the present invention by aspartic acid.

Sensitivity to aspartic acid was investigated in accordance with a known method (Yoshinaga, T., Izui, K. and Katsuki, H., J. Biochem., 68, 747–750 (1970)). Namely, as a result of measurement of the enzyme activity produced by each of the transformants or Escherichia coli harboring pS2 in the presence of acetyl-coenzyme A known to affect the activity in an activity measurement system at a concentration of 0.1 mM or 1 mM, sensitivity to aspartic acid was measured as shown in FIGS. 9 and 10.

According to the result, it is apparent that the wild type enzyme loses its activity when aspartic acid is at a high concentration, while the mutant phosphoenolpyruvate carboxylase of the present invention substantially continues to maintain its activity.

EXAMPLE 3

Fermentative Production of L-threonine by Escherichia Coli with Introduced Mutant Phosphoenolpyruvate Carboxylase As threonine-producing bacteria of Escherichia coli, B-3996 strain (Japanese Patent Laid-open No. 3-501682 (PCT)) has the highest production ability among those known at present. Thus upon evaluation of the mutant phosphoenolpyruvate carboxylase, B-3996 was used as the host. This B-3996 strain has been deposited in Research Institute for Genetics and Industrial Microorganism Breeding under a registration number of RIA 1867. Further, pBP5 was selected as the mutant phosphoenolpyruvate carboxylase to be evaluated, which was subjected to an experiment.

The plasmid pBP5 having the mutant phosphoenolpyruvate carboxylase was introduced into Escherichia coli B-3996 in accordance with a method of Hanahan (J. Mol. Biol., Vol. 106, p577 (1983)), and a transformant was isolated. As a control, Escherichia coli B-3996 was transformed in the same manner with pS2 as the plasmid to express the wild type phosphoenolpyruvate carboxylase gene.

When Escherichia coli B-3996 and the transformants therefrom were respectively inoculated in a 500 ml of Sakaguchi flask poured with 20 ml of a medium having a composition in Table 3, and cultivated at 37° C. for 40 hours to investigate a production amount of L-threonine, then results shown in Table 4 were obtained. Incidentally, the aforementioned medium was separated into two: glucose and $MgSO_4 \cdot 7H_2O$, and the other components, and adjusted to have a pH of 7.0 with KOH followed by autoclaving at 115° C. for 10 minutes, and then, after mixing them, separately sterilized $CaCO_3$ was added by 30 g/l.

TABLE 3

| Component | Blending amount (g/l) |
|---|---|
| glucose | 40 |
| $(NH_4)_2SO_4$ | 16 |
| $KH_2PO_4$ | 1 |
| $MgSO_4 \cdot 7H_2O$ | 1 |
| $FeSO_4 \cdot 7H_2O$ | 0.01 |
| $MnSO_4 \cdot 5H_2O$ | 0.01 |
| yeast extract (Difco) | 2 |
| L-Met | 0.5 |
| $CaCO_3$ | 30 |

TABLE 4

| Bacterial strain | Threonine production amount (g/l) |
|---|---|
| Escherichia coli B-3996 | 15.7 |
| Escherichia coli B-3996/pS2 | 15.8 |
| Escherichia coli B-3996/pBP5 | 16.8 |

As clarified from the result, Escherichia coli B-3996/pBP5 harboring the mutant enzyme expression plasmid having the DNA sequence of the present invention had an improved threonine-producing ability as compared with Escherichia coli B-3996/pS2 harboring the plasmid to express the wild type enzyme.

EXAMPLE 4

Fermentative Production of L-glutamic Acid by Escherichia Coli with Introduced Mutant Phosphoenolpyruvate Carboxylase As glutamic acid-producing bacteria of Escherichia coli, Escherichia coli AJ-12628 described in Japanese Patent Laid-open No. 4-11461 has the highest production ability among those known at present. Thus upon evaluation of the mutant phosphoenolpyruvate carboxylase, AJ-12628 was used as the host.

The AJ-12628 strain has been deposited in National Institute of Bioscience and Human Technology of Agency of Industrial Science and Technology under a registration number of FERM BP-385 Further, pBP5 was selected as the mutant phosphoenolpyruvate carboxylase to be evaluated, which was subjected to an experiment.

The plasmid pBP5 having the mutant phosphoenolpyruvate carboxylase was introduced into Escherichia coli AJ-12628 in accordance with a method of Hanahan (J. Mol.

*Biol.*, Vol. 106, p577 (1983)), and a transformant was isolated. In the same manner, a transformant of *Escherichia coli* AJ-*12628* with pS2 was isolated.

When *Escherichia coli* AJ-12628 and the transformants therefrom were respectively inoculated in a 500 ml of Sakaguchi flask poured with 20 ml of a medium having a composition in Table 5, and cultivated at 37° C. for 36 hours to investigate a production amount of L-glutamic acid, then results shown in Table 6 were obtained. Incidentally, the aforementioned medium was separated into two: glucose and $MgSO_4.7H_2O$, and the other components, and adjusted to have a pH of 7.0 with KOH followed by autoclaving at 115° C. for 10 minutes, and then, after mixing them, separately sterilized $CaCO_3$ was added by 30 g/l.

TABLE 5

| Component | Blending amount (g/l) |
|---|---|
| glucose | 40 |
| $(NH_4)_2SO_4$ | 16 |
| $KH_2PO_4$ | 1 |
| $MgSO_4.7H_2O$ | 1 |
| $FeSO_4.7H_2O$ | 0.01 |
| $MnSO_4.5H_2O$ | 0.01 |
| yeast extract (Difco) | 2 |
| $CaCO_3$ | 30 |

TABLE 6

| Bacterial strain | Glutamic acid production amount (g/l) |
|---|---|
| *Escherichia coli* AJ-12628 | 18.0 |
| *Escherichia coli* AJ-12628/pS2 | 18.3 |
| *Escherichia coli* AJ-12628/pBP5 | 19.6 |

As clarified from the result, *Escherichia coli* AJ-12628/pBP5 harboring the mutant enzyme expression plasmid having the DNA sequence of the present invention had an improved glutamate-producing ability as compared with *Escherichia coli* AJ-12628/pS2 harboring the plasmid to express the wild type enzyme.

EXAMPLE 5

Production of L-lysine by Coryneform Bacterium with Introduced Mutant Phosphoenolpyruvate Carboxylase In order to introduce and express the mutant gene in a coryneform bacterium, a promoter originating from a bacterium belonging to the genus Brevibacterium was obtained, and was ligated with the mutant gene to prepare an expression type plasmid. Further, it was introduced into a bacterium belonging to the genus Brevibacterium to perform production of L-lysine.

<1> Acquisition of Aspartokinase (AK) Gene Originating from Bacterium Belonging to the Genus Brevibacterium Chromosomal DNA was prepared according to an ordinary method from a *Brevibacterium lactofermentum* (*Corynebacterium glutamicum*) wild strain (ATCC 13869). An AK gene was amplified from the chromosomal DNA by PCR (polymerase chain reaction; see White, T. J. et al., *Trends Genet.*, 5, 185 (1989)). For DNA primers used in the amplification, an oligonucleotide of 23 mer (SEQ ID NO:3) and an oligonucleotide of 21 mer (SEQ ID NO:4) were synthesized to amplify a region of about 1643 bp coding for the AK gene based on a sequence known in *Corynebacterium glutamicum* (see *Molecular Microbiology* (1991) 5 (5), 1197–1204, *Mol. Gen. Genet.* (1990) 224, 317–324).

The synthesis of DNA was performed in accordance with an ordinary phosphoamidite method (see *Tetrahedron Letters* (1981), 22, 1859) using a DNA synthesizer model 380B produced by Applied Biosystems Co. In the PCR reaction, DNA Thermal Cycler PJ2000 type produced by Takara Shuzo Co., Ltd. was used, and gene amplification was performed by using Taq DNA polymerase in accordance with a method designated by the manufacturer.

An amplified gene fragment of 1643 kb was confirmed by agarose gel electrophoresis, and then the fragment cut out from the gel was purified by an ordinary method, and was cleaved with restriction enzymes NruI (produced by Takara Shuzo Co., Ltd.) and EcoRI (produced by Takara Shuzo Co., Ltd.). pHSG399 (see Takeshita, S. et al.; *Gene* (1987), 61, 63–74) was used for a cloning vector for the gene fragment. pHSG399 was cleaved with a restriction enzyme SmaI (produced by Takara Shuzo Co., Ltd.) and a restriction enzyme EcoRI, and ligated with the amplified AK gene fragment.

Ligation of DNA was performed by a designated method by using a DNA ligation kit (produced by Takara Shuzo Co., Ltd.). In such a manner, a plasmid was manufactured in which pHSG399 was ligated with the AK gene fragment amplified from Brevibacterium chromosome. The plasmid having the AK gene originating from ATCC 13869 as the wild strain was designated as p399AKY.

<2> Determination of Base Sequence of AK Gene of *Brevibacterium lactofermentum*

The AK plasmid, p399AKY was prepared, and the base sequence of the AK gene was determined. Determination of the base sequence was performed in accordance with the method of Sanger et al. (F. Sanger et al.: *Proc. Natl. Acad. Sci. USA*, 74, 5463 (1977) and so forth). Results are shown in SEQ ID NO:5 and SEQ ID NO:7. The DNA fragments have two open reading frames which correspond to α-subunit and β-subunit of AK, respectively. In SEQ ID NO:5 and SEQ ID NO:7, amino acid sequences corresponding to each of the open reading frames are shown together with nucleotide sequences. Further, only the amino acid sequences corresponding to each of the open reading frames are shown in SEQ ID NO:6 and SEQ ID NO:8.

<3> Preparation of Phosphoenolpyruvate Carboxylase Expression Plasmid

SalI fragments of about 4.4 kb containing phosphoenolpyruvate carboxylase genes were extracted from pS2 as the plasmid having the wild type phosphoenolpyruvate carboxylase gene and pBP5 as the plasmid having the obtained mutant phosphoenolpyruvate carboxylase gene, and inserted into a SalI site of a plasmid vector pHSG399 universally used for *Escherichia coli*. Manufactured plasmids were designated as pHS2 for the wild type and as pHBP5 for the mutant.

In order to convert pHS2 and pHPB5 into plasmids to express in Brevibacterium, a promoter and a replication origin of a plasmid for functioning in Brevibacterium were introduced. As the promoter, a gene fragment containing one from 1st NruI site to 207th ApaLI site of the base sequence, which was postulated to be a promoter region of the cloned AK gene, was extracted from p399AXY, and inserted into an AvaI site located about 60 bp before the structural genes of pHS2 and pHBP5 to allow the transcription direction to be in a regular direction.

Further, a gene fragment to enable autonomously replication of the plasmid in Brevibacterium, namely the replication origin of the plasmid was introduced into a site located on the vector. A gene fragment containing the replication origin of the plasmid was extracted from a vector pHC4 for Brevibacterium (see paragraph No. 10 in Japanese Patent Laid-open No. 5-7491; *Escherichia coli* AJ12039 harboring the same plasmid is deposited in National Institute of Bioscience and Human Technology of Agency of Industrial Science and Technology, to which a deposition number of FERM P12215 is given), and restriction enzyme sites at both termini were modified into PstI sites by introduction of linkers.

This fragment was introduced into a PstI site in a vector portion of the plasmid added with the promoter derived from Brevibacterium. Constructed phosphoenolpyruvate carboxylase-expressing plasmids were designated as pHS2B for a wild type phosphoenolpyruvate carboxylase plasmid originating from pS2 and as pHBP5B for a mutant phosphoenolpyruvate carboxylase plasmid originating from pBP5, respectively.

<4> Production of L-lysine by Using Phosphoenolpyruvate Carboxylase Expression Type Plasmid Prepared pHS2B and pHBP5B were respectively introduced into AJ3463 as an L-lysine-producing bacterium of *Brevibacterium lactofermentum* (see Japanese Patent Publication No. 51-34477). For introduction of the gene, a transformation method employing electric pulse was used (see Japanese Patent Laid-open No. 2-207791). The host strain and transformants were cultivated with shaking for 72 hours at 31.5° C. in a lysine production medium having a composition in Table 7. The aforementioned medium was prepared such that those except for $CaCO_3$ among the components listed in the table were added to 1 l of water, and adjusted to have a pH of 8.0 with KOH followed by autoclaving at 115° C. for 15 minutes, and then $CaCO_3$ having been subjected to heat sterilization was further added. Accumulated amounts of L-lysine in the medium after cultivation are shown in Table 8.

TABLE 7

| Component | Blending amount in 1 L | |
|---|---|---|
| glucose | 100 | g |
| $(NH_4)_2SO_4$ | 55 | g |
| soybean concentrate* | 35 | ml |
| $KH_2PO_4$ | 1 | g |
| $MgSO_4.7H_2O$ | 1 | g |
| vitamin B1 | 20 | g |
| biotin | 5 | g |
| nicotinic acid amide | 5 | mg |
| $FeSO_4.7H_2O$ | 0.01 | g |
| $MnSO_4.5H_2O$ | 0.01 | g |
| $CaCO_3$ | 50 | g |

*product of Ajinomoto Co., Ltd. (trade name: Mamenou)

TABLE 8

| Bacterial strain | Lysine production amount (g/l) |
|---|---|
| *Brevibacterium lactofermentum* AJ3463 | 20.0 |
| *Brevibacterium lactofermentum* AJ3463/pHS2B | 22.0 |
| *Brevibacterium lactofermentum* AJ3463/pHBP5B | 25.0 |

As shown in the result, *Brevibacterium lactofermentum* AJ3463/pHBP5B harboring the mutant enzyme expression plasmid having the DNA sequence of the present invention had an improved lysine-producing ability as compared with *Brevibacterium lactofermentum* AJ3463/pHS2B harboring the plasmid to express the wild type enzyme.

EXAMPLE 6

Another Example of Mutant Phosphoenolpyruvate Carboxylase of the Present Invention and its Gene <1> Preparation of Mutant Phosphoenolpyruvate Carboxylase Gene Upon preparation of DNA coding for a mutant phosphoenolpyruvate carboxylase, a phosphoenolpyruvate carboxylase gene cloned in a plasmid pT2 was used as a material.

A host, which is allowed to harbor the plasmid pT2, is preferably deficient in phosphoenolpyruvate carboxylase gene in order to detect only the activity of phosphoenolpyruvate carboxylase originating from the plasmid. *Escherichia coli* F15 (Hfr, recA1, met, Δ(ppc-argECBH), Tn10) was used as such a deficient strain. *Escherichia coli* AJ-12873, which is allowed to harbor pT2 in F15 strain, is deposited as FERM P-13752 in National Institute of Bioscience and Human Technology of Agency of Industrial Science and Technology (1-3, Higashi 1-chome, Tsukuba-shi, Ibaraki-ken, Japan; zip code 305) on Jul. 15, 1993, transferred from the original deposition to international deposition based on Budapest Treaty on Jul. 11, 1994 and has been deposited as deposition number of FERM BP-4732. In addition, an entire base sequence of pT2 is shown in SEQUENCE ID NO:1.

In order to replace a codon of 438th arginine of the phosphoenolpyruvate carboxylase into a codon of cysteine by using pT2, the Overlapping Extension method (Ho, S. N., Hunt, H. D., Horton, R. M., Pullen, J. K. and Pease, L. R., *Gene*, 77, 51–59 (1989)) utilizing the PCR (Polymerase Chain Reaction) method was used.

Incidentally, the PCR method is a method in which an amplification cycle comprising thermal denaturation of double strand DNA into single strand DNA, annealing of oligonucleotide primers corresponding to sequences at both ends of a site aimed to be amplified and the aforementioned thermally denatured DNA, and polymerase reaction using the aforementioned oligonucleotides as primers is repeated, thereby the aforementioned DNA sequence is amplified in a manner of an exponential function.

Figure 11:
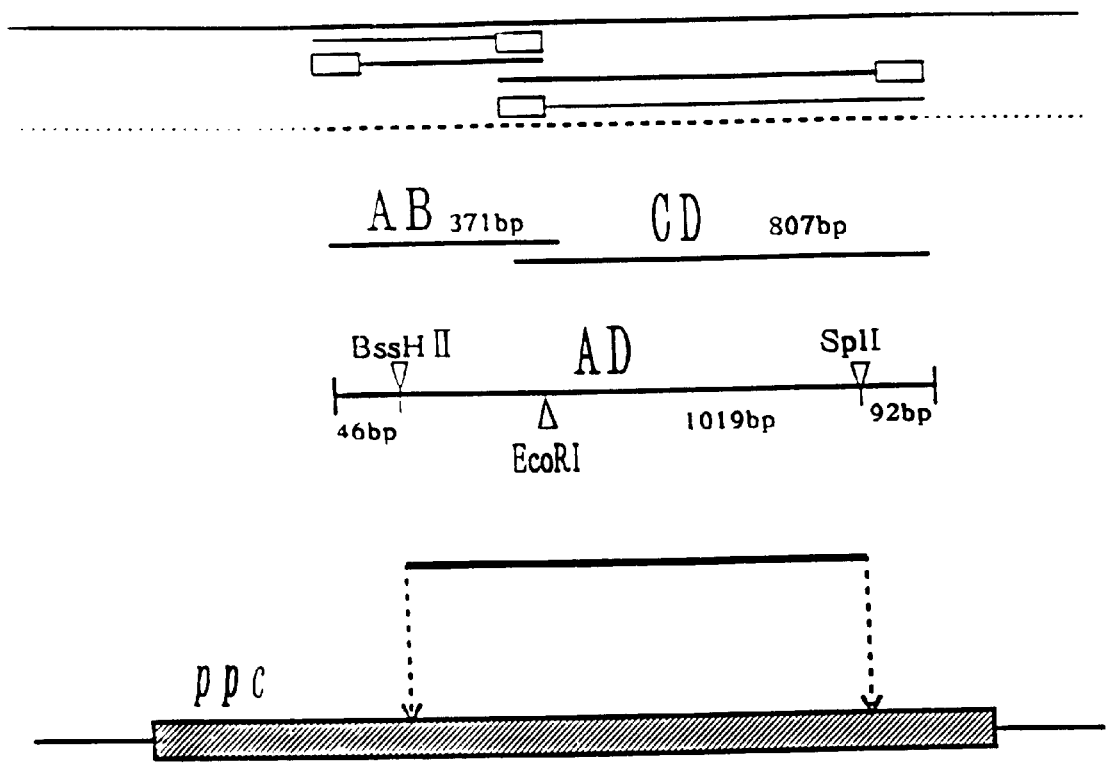
FIG. 11 shows a method for introducing mutation into a phosphoenolpyruvate carboxylase gene.

A region subjected to site specific mutation by the PCR method is shown in FIG. 11. The primers used in the present invention were 4 species of a primer c (SEQUENCE ID NO:11, corresponding to base Nos. 1535–1554 in SEQUENCE ID NO:1) having a sequence in the vicinity of the codon of 438th arginine, a primer b (SEQUENCE ID NO:10) having a sequence complement to the primer c, a primer a (SEQUENCE ID NO:9, corresponding to base Nos. 1185–1200 in SEQUENCE ID NO:1) having a sequence upstream therefrom, and a primer d (SEQUENCE ID NO:12, corresponding to base Nos. 2327–2342 in SEQUENCE ID NO:1) having a sequence complement to a downstream sequence.

In the primer b and the primer c, the codon (CGT) of 438th arginine was replaced with a codon (TGT) of cysteine. This replacement may use TGC which is another codon of cysteine. Further, C of the third letter of a codon (AAC) of 435th asparagine was replaced with T, and hence an EcoRI site was internally introduced with no replacement of amino acid, so that a mutant plasmid could be selected by using it as an index. However, this mutation is not essential to the present invention.

When the PCR reaction was performed by using pT2 DNA as a template and the primer a and the primer b as the primers, a fragment from the upstream of the mutation site to the mutation site (AB fragment in FIG. 11) was amplified. Further, when the PCR reaction was performed by using the primer c and the primer d, a fragment downstream from the mutation site (CD fragment in FIG. 11) was amplified. When each of the amplified products (AB, CD) was annealed again after thermal denaturation to perform a polymerase reaction, they were ligated to obtain a fragment (AD fragment in FIG. 11). Incidentally, the PCR reaction was performed by repeating 30 cycles of each comprising heating at 94° C. for 1 minute followed by denaturation (94° C., 1.5 minutes), annealing (50° C., 2 minutes), and elongation reaction by polymerase (72° C., 3.5 minutes). In addition, reaction compositions are shown in Table 9.

TABLE 9

| Composition | PCR fragment | | |
|---|---|---|---|
| (( ): final conc.) | AB | CD | AD |
| $H_2O$ | 53.5 | 53.5 | 53.5 |
| 10-fold reaction buffer | 10 | 10 | 10 |
| mixture of 1.25 mM dNTP | 16 | 16 | 16 |
| 20 µM primer a (1 µM) | 5 | — | 5 |
| 20 µM primer b (1 µM) | 5 | — | — |
| 20 µM primer c (1 µM) | — | 5 | — |
| 20 µM primer d (1 µM) | — | 5 | 5 |
| 10 µg/µl pT2 (0.1 µg) | 10 | 10 | — |
| PCR fragment AB* | — | — | 5 |
| PCR fragment CD* | — | — | 5 |
| 2.5 U/µl Taq polymerase | 0.5 | 0.5 | 0.5 |
| total amount | 100 µl | 100 µl | 100 µl |

*PCR fragments AB and CD were prepared, after the PCR reaction, by recovering 10 µl thereof from polyacrylamide gel, and dissolving it in 5 µl of TE (10 mM Tris-HCl (pH 8.0), 1 mM EDTA (pH 8.0)).

In the AD fragment obtained as described above, a BssHII site (1231–1236 in SEQ ID NO:1) at the upstream side and a SplI site (2249–2254 in SEQ ID NO:1) at the downstream side were present, so that complete digestion was performed with these enzymes to make replacement for a corresponding region of the plasmid pT2 (FIG. 11).

<2> Selection of Inhibition-desensitized Phosphoenolpyruvate Carboxylase

*Escherichia coli* was transformed with a plasmid obtained as described above, and a transformed strain was cultivated to recover the plasmid to select one cleaved by EcoRI. With respect to selected DNA, a base sequence of the region amplified by the aforementioned PCR method was determined by the dideoxy method to confirm that base replacement as exactly aimed was introduced. This plasmid was designated as pT2R438C. A strain (AJ12874) obtained by introducing this plasmid into the aforementioned *Escherichia coli* F15 has been deposited as FERM P-13753 in National Institute of Bioscience and Human Technology of Agency of Industrial Science and Technology (1-3, Higashi 1-chome, Tsukuba-shi, Ibaraki-ken, Japan; zip code 305) on Jul. 15, 1993, transferred from the original deposition to international deposition based on Budapest Treaty on Jul. 11, 1994 and has been deposited as deposition number of FERM BP-4733.

The base sequence of pT2R438C is a sequence in which 1541th and 1550th nucleotides are replaced from C to T respectively in SEQ ID NO:1.

<3> Confirmation of Desensitization of Inhibition of Mutant Phosphoenolpyruvate Carboxylase by Aspartic Acid Sensitivity to aspartic acid was investigated for phosphoenolpyruvate carboxylase produced by the aforementioned *Escherichia coli* AJ12874 harboring pT2R438C. Incidentally, as described above, because the *Escherichia coli* F15 is deficient in phosphoenolpyruvate carboxylase, phosphoenolpyruvate carboxylase produced by AJ12874 originates from the plasmid.

Figure 12A:
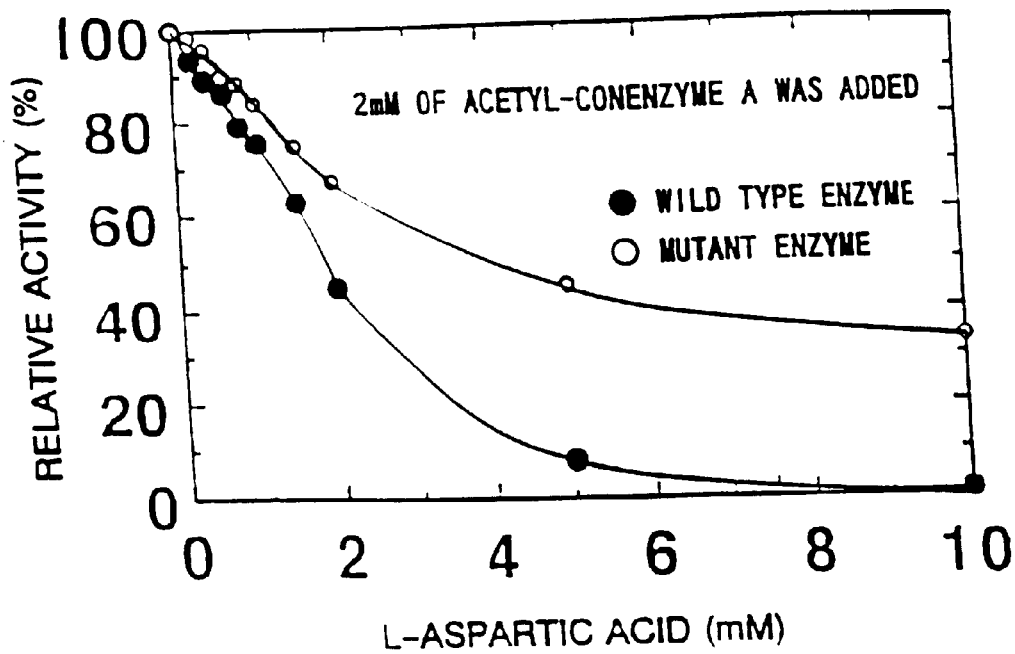
FIG. 12 shows influences exerted by aspartic acid on activities of wild type and mutant phosphoenolpyruvate carboxylase in which 438th arginine was substituted with cysteine counted from the N-terminus.
Figure 12B:
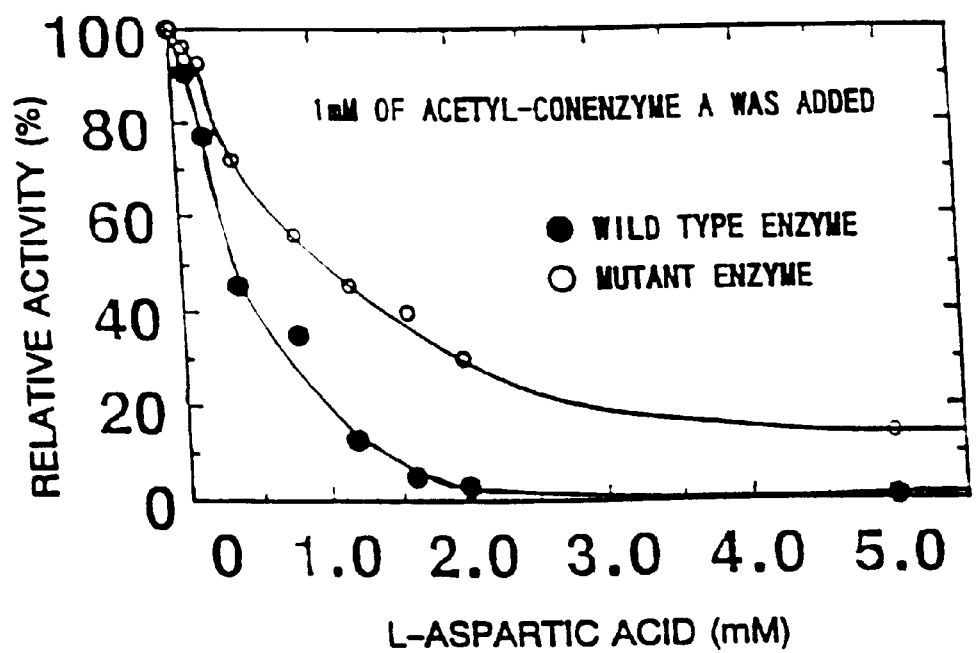

Sensitivity to aspartic acid was investigated in accordance with a known method (Yoshinaga, T., Izui, K. and Katsuki, H., *J. Biochem.*, 68, 747–750 (1970)). Namely, as a result of measurement of the enzyme activity in the presence of acetyl-coenzyme A known to affect the activity in an activity measurement system at a concentration of 1 mM or 2 mM, sensitivity to aspartic acid was measured as shown in FIG. 12.

It is apparent that the wild type enzyme substantially loses its activity when aspartic acid is at a high concentration, while the mutant phosphoenolpyruvate carboxylase of the present invention continues to maintain its activity.

<4> Preparation of Mutant Phosphoenolpyruvate Carboxylase Gene (II)

In order to replace a codon of 620th lysine with a codon of serine in the phosphoenolpyruvate carboxylase gene carried on the plasmid pT2, the Overlapping Extension method (Ho, S. N., Hunt, H. D., Horton, R. M., Pullen, J. K. and Pease, L. R., *Gene*, 77, 51–59 (1989)) utilizing the PCR (Polymerase Chain Reaction) method was used. Concrete procedures were in accordance with the method described in <1>. A plasmid carrying a mutant gene constructed with aimed replacement was designated as pT2K620S. Further, an obtained mutant enzyme was designated as K620S mutant enzyme.

<5> Confirmation of Desensitization of Inhibition by Aspartic Acid Concerning Mutant Phosphoenolpyruvate Carboxylase.

With respect to the phosphoenolpyruvic carboxylase produced by a transformant obtained by introducing the plasmid pT2K620S into the aforementioned *Escherichia coli* F15, sensitivity to aspartic acid was investigated. Incidentally, as described above, since the *Escherichia coli* F15 lacks phosphoenolpyruvate carboxylase, any phosphoenolpyruvate carboxylase produced by the transformant originates from the plasmid.

Sensitivity to aspartic acid was investigated in accordance with a known method (Yoshinaga, T., Izui, K. and Katsuki, H., *J. Biochem.*, 68, 747–750 (1970)). Namely, as a result of measurement of the enzyme activity in the presence of acetyl-coenzyme A known to affect the activity in an activity measurement system at a concentration of 1 mM or 2 mM, sensitivity to aspartic acid was measured as shown in FIG. 13.

It is apparent that the wild enzyme substantially loses its activity when aspartic acid is at a high concentration, while the type phosphoenolpyruvate carboxylase of the present invention continues to maintain its activity.

Figure 13A:
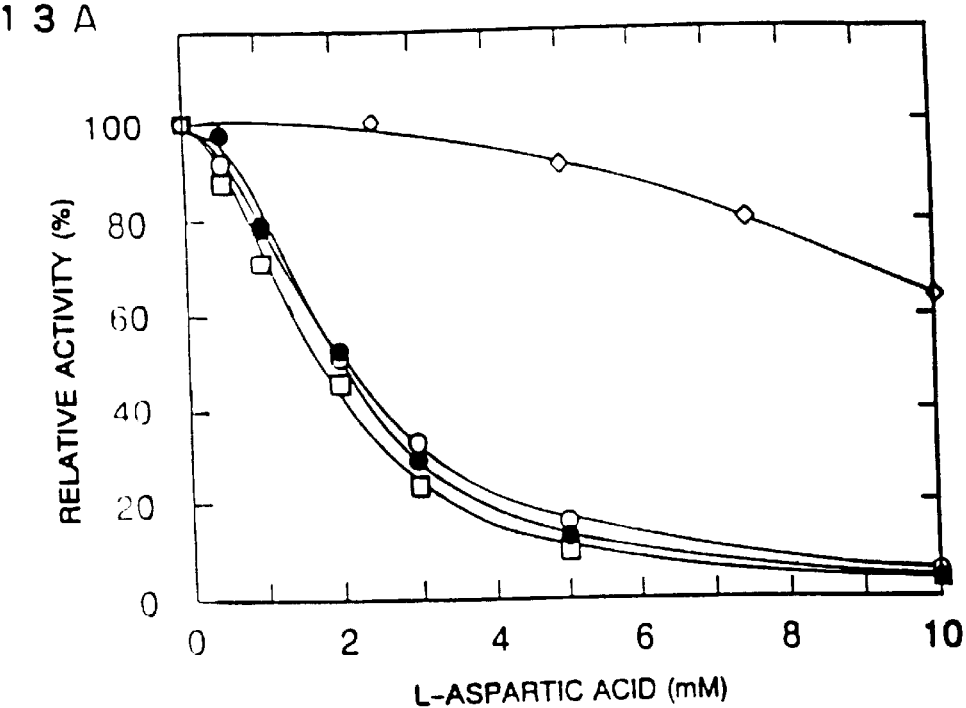
FIG. 13 shows the influence exerted by (a) 1–10 mM aspartic acid and (b) 1–50 mM aspartic acid on the activities of the wild-type *E. coli phosphoenopyruvate carboxylase* (solid circles) and the mutants K491A (open squares), K605A (open circles), and K620S (open diamonds).
Figure 13B:
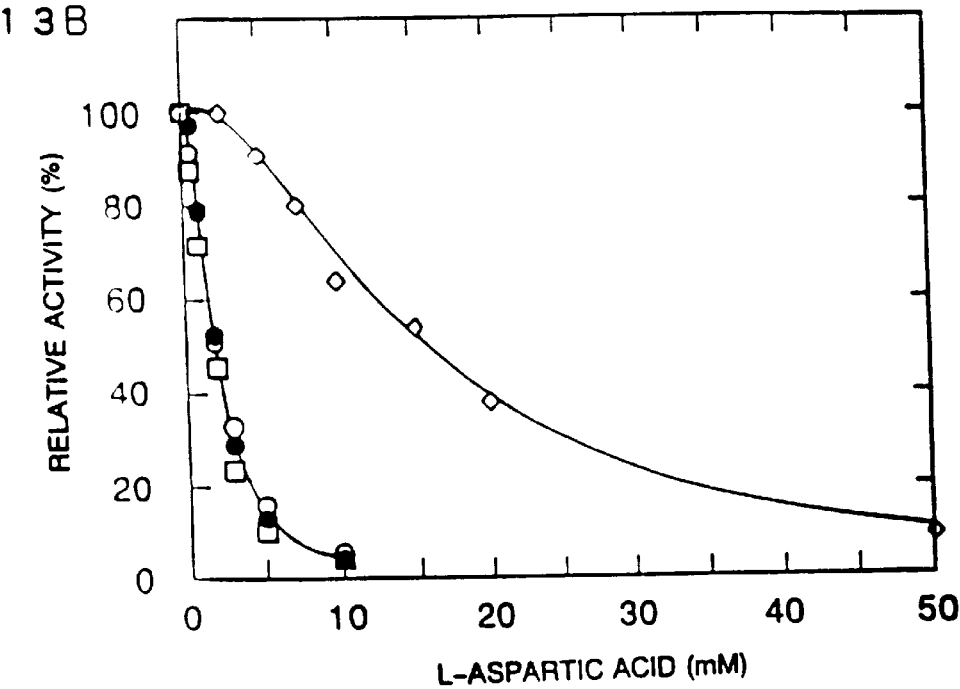

In FIG. 13, sensitivity to aspartic acid is also depicted for a mutant phosphoenolpyruvate carboxylase in which 650th lysine is replaced with serine (K650A mutant enzyme), and for a mutant phosphoenolpyruvate carboxylase in which 491th lysine is replaced with serine (K491A mutant enzyme). In the case of these mutant enzymes, inhibition by aspartic acid was not desensitized.

INDUSTRIAL APPLICABILITY

The DNA sequence of the present invention codes for the mutant phosphoenolpyruvate carboxylase, and the microorganism harboring this DNA sequence produces the aforementioned enzyme.

The mutant phosphoenolpyruvate carboxylase of the present invention does not substantially undergo activity inhibition by aspartic acid, so that it can be utilized for fermentative production of amino acids subjected to regulation of biosynthesis by aspartic acid and the like.

What is claimed is:

1. An isolated DNA fragment which codes for a mutant phosphoenolpyruvate carboxylase of SEQ ID NO:2, wherein said mutant phosphoenolpyruvate carboxylate has a mutation to desensitize feedback inhibition of the phosphoenolpyruvate carboxylase by aspartic acid, wherein said mutation is at least one selected from the group consisting of:
(i) mutation of the glutamic acid residue at the 625th position of SEQ ID NO:2 to an amino acid residue other than glutamic acid;
(ii) mutation of the arginine residue at the 222nd position of SEQ ID NO:2 and the glutamic acid residue at the 223rd position of SEQ ID NO:2 to an amino acid residue other than arginine and an amino acid residue other than glutamic acid, respectively;
(iii) mutation of the serine residue at the 288th position of SEQ ID NO:2, the glutamic acid residue at the 289th position of SEQ ID NO:2, the methionine residue at the 551st position of SEQ ID NO:2 and the glutamic acid residue at the 804th position of SEQ ID NO:2 to an amino acid residue other than serine, an amino acid residue other than glutamic acid, an amino acid residue other than methionine and an amino acid residue other than glutamic acid, respectively;
(iv) mutation of the alanine residue at the 867th position of SEQ ID NO:2 to an amino acid residue other than alanine;
(v) mutation of the arginine residue at the 438th position of SEQ ID NO:2 to an amino acid residue other than arginine; and
(vi) mutation of the lysine residue at the 620th position of SEQ ID NO:2 to an amino acid residue other than lysine, and
each of said positions is a position from the N-terminus of said mutant phsphoenolpyruvate carboxylase.

2. A microorganism belonging to the genus Escherichia or coryneform bacteria, transformed by integration of the DNA fragment as defined in claim 1 into the chromosomal DNA of said microorganism.

3. A recombinant DNA formed by ligating the DNA fragment as defined in claim 1 with a vector DNA capable of autonomously replication in cells of bacteria belonging to the genus Escherichia or coryneform bacteria.

4. A microorganism belonging to the genus Escherichia or coryneform bacteria, transformed with the recombinant DNA as defined in claim 3.

5. The DNA fragment according to claim 1 wherein said mutation is at least one selected from the group consisting of:
(i) mutation of the glutamic acid residue at the 625th position of SEQ ID NO:2 to a lysine residue;
(ii) mutation of the arginine residue at the 222nd position of SEQ ID NO:2 and the glutamic acid residue at the 223rd position of SEQ ID NO:2 to a histidine residue and a lysine residue, respectively;

(iii) mutation of the serine residue at the 288th position of SEQ ID NO:2, the glutamic acid residue at the 289th postion of SEQ ID NO:2, the methionine residue at the 551st position of SEQ ID NO:2 and the glutamic acid residue at the 804th position of SEQ ID NO:2 to a phenylalanine residue, a lysine residue, an isoleucine residue and a lysine residue, respectively;

(iv) mutation of the alanine residue at the 867th position of SEQ ID NO:2 to a threonine residue;

(v) mutation of the arginine residue at the 438th position of SEQ ID NO:2 to a cysteine residue; and (vi) mutation of the lysine residue at the 620th position of SEQ ID NO:2 to a serine residue.

6. The DNA fragment according to claim 5, wherein said mutation is mutation of the glutamic acid residue at the 625th position of SEQ ID NO:2 to a lysine residue.

7. The DNA fragment according to claim 5, wherein said mutation is mutation of the arginine residue at the 222th position of SEQ ID NO:2 and the glutamic acid residue at the 223rd position of SEQ ID NO:2 to a histidine residue and a lysine residue respectively.

8. The DNA fragment according to claim 5, wherein said mutation is mutation of the serine residue at the 288th position of SEQ ID NO:2, the glutamic acid residue at the 289th position of SEQ ID NO:2, the methionine residue at the 551st position of SEQ ID NO:2 and the glutamic acid residue at the 804th position of SEQ ID NO:2 to a phenylalanine residue, a lysine residue, an isoleucine residue and a lysine residue, respectively.

9. The DNA fragment according to claim 5, wherein said mutation is mutation of the alanine residue at the 867th position of SEQ ID NO:2 to a threonine residue.

10. The DNA fragment according to claim 5, wherein said mutation is mutation of the lysine residue at the 438th position of SEQ ID NO:2 to a cysteine residue.

11. The DNA fragment according to claim 5, wherein said mutation is mutation of the lysine residue at the 620th position of SEQ ID NO:2 to a serine residue.

12. The DNA fragment according to claim 5, wherein said mutation is mutation of the glutamic acid residue at the 625th position of SEQ ID NO:2 to an amino acid residue other than glutamic acid.

13. The DNA fragment according to claim 5, wherein said mutation is mutation of the arginine residue at the 222nd position of SEQ ID NO:2 and the glutamic acid residue at the 223rd position of SEQ ID NO:2 to an amino acid residue other than arginine and an amino acid residue other than glutamic acid respectively.

14. The DNA fragment according to claim 5, wherein said mutation is mutation of the serine residue at the 288th position of SEQ ID NO:2, the glutamic acid residue at the 289th position of SEQ ID NO:2, the methionine residue at the 551st position of SEQ ID NO:2 and the glutamic acid residue at the 804th position of SEQ ID NO:2 to an amino acid residue other than serine, an amino acid residue other than glutamic acid an amino acid residue other than methionine and an amino acid residue other than glutamic acid, respectively.

15. The DNA fragment according to claim 5, wherein said mutation is mutation of the alanine residue at the 867th position of SEQ ID NO:2 to an amino acid residue other than alanine.

16. The DNA fragment according to claim 5, wherein said mutation is mutation of the arginine residue at the 438th position of SEQ ID NO:2 to an amino acid residue other than arginine.

17. The DNA fragment according to claim 5, wherein said mutation is mutation of the lysine residue at the 620th position of SEQ ID NO:2 to an amino acid residue other than lysine.

* * * * *

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
    (A) LENGTH: 5186 base pairs
    (B) TYPE: nucleic acid
    (C) STRANDEDNESS: double
    (D) TOPOLOGY: circular (ii) MOLECULE TYPE: DNA (genomic)

(iv) ANTI-SENSE: NO (vi) ORIGINAL SOURCE:
    (A) ORGANISM: Escherichia coli (ix) FEATURE:
    (A) NAME/KEY: CDS
    (B) LOCATION: 237..2888

(xi) SEQUENCE DESCRIPTION: SEQ ID NO:1:

```
TCGACCGGCG ATTTTTTAAC ATTTCCATAA GTTACGCTTA TTTAAAGCGT CGTGAATTTA      60

ATGACGTAAA TTCCTGCTAT TTATTCGTTT GCTGAAGCGA TTTCGCAGCA TTTGACGTCA     120

CCGCTTTTAC GTGGCTTTAT AAAAGACGAC GAAAAGCAAA GCCCGAGCAT ATTCGCGCCA     180

ATGCGACGTG AAGGATACAG GGCTATCAAA CGATAAGATG GGGTGTCTGG GGTAAT        236

ATG AAC GAA CAA TAT TCC GCA TTG CGT AGT AAT GTC AGT ATG CTC GGC       284
Met Asn Glu Gln Tyr Ser Ala Leu Arg Ser Asn Val Ser Met Leu Gly
  1               5                  10                  15

AAA GTG CTG GGA GAA ACC ATC AAG GAT GCG TTG GGA GAA CAC ATT CTT       332
Lys Val Leu Gly Glu Thr Ile Lys Asp Ala Leu Gly Glu His Ile Leu
             20                  25                  30

GAA CGC GTA GAA ACT ATC CGT AAG TTG TCG AAA TCT TCA CGC GCT GGC       380
Glu Arg Val Glu Thr Ile Arg Lys Leu Ser Lys Ser Ser Arg Ala Gly
         35                  40                  45

AAT GAT GCT AAC CGC CAG GAG TTG CTC ACC ACC TTA CAA AAT TTG TCG       428
Asn Asp Ala Asn Arg Gln Glu Leu Leu Thr Thr Leu Gln Asn Leu Ser
     50                  55                  60

AAC GAC GAG CTG CTG CCC GTT GCG CGT GCG TTT AGT CAG TTC CTG AAC       476
Asn Asp Glu Leu Leu Pro Val Ala Arg Ala Phe Ser Gln Phe Leu Asn
 65                  70                  75                  80

CTG GCC AAC ACC GCC GAG CAA TAC CAC AGC ATT TCG CCG AAA GGC GAA       524
Leu Ala Asn Thr Ala Glu Gln Tyr His Ser Ile Ser Pro Lys Gly Glu
                 85                  90                  95

GCT GCC AGC AAC CCG GAA GTG ATC GCC CGC ACC CTG CGT AAA CTG AAA       572
Ala Ala Ser Asn Pro Glu Val Ile Ala Arg Thr Leu Arg Lys Leu Lys
            100                 105                 110

AAC CAG CCG GAA CTG AGC GAA GAC ACC ATC AAA AAA GCA GTG GAA TCG       620
Asn Gln Pro Glu Leu Ser Glu Asp Thr Ile Lys Lys Ala Val Glu Ser
        115                 120                 125

CTG TCG CTG GAA CTG GTC CTC ACG GCT CAC CCA ACC GAA ATT ACC CGT       668
Leu Ser Leu Glu Leu Val Leu Thr Ala His Pro Thr Glu Ile Thr Arg
    130                 135                 140

CGT ACA CTG ATC CAC AAA ATG GTG GAA GTG AAC GCC TGT TTA AAA CAG       716
Arg Thr Leu Ile His Lys Met Val Glu Val Asn Ala Cys Leu Lys Gln
145                 150                 155                 160

CTC GAT AAC AAA GAT ATC GCT GAC TAC GAA CAC AAC CAG CTG ATG CGT       764
Leu Asp Asn Lys Asp Ile Ala Asp Tyr Glu His Asn Gln Leu Met Arg
                165                 170                 175
```

| | | | | | | | | | | | | | | |
|---|---|---|---|---|---|---|---|---|---|---|---|---|---|---|
| CGC | CTG | CGC | CAG | TTG | ATC | GCC | CAG | TCA | TGG | CAT | ACC | GAT | GAA | ATC | CGT | 812 |
| Arg | Leu | Arg | Gln | Leu | Ile | Ala | Gln | Ser | Trp | His | Thr | Asp | Glu | Ile | Arg |
| | | | 180 | | | | | 185 | | | | | 190 | | |

```
CGC CTG CGC CAG TTG ATC GCC CAG TCA TGG CAT ACC GAT GAA ATC CGT      812
Arg Leu Arg Gln Leu Ile Ala Gln Ser Trp His Thr Asp Glu Ile Arg
            180                 185                 190

AAG CTG CGT CCA AGC CCG GTA GAT GAA GCC AAA TGG GGC TTT GCC GTA      860
Lys Leu Arg Pro Ser Pro Val Asp Glu Ala Lys Trp Gly Phe Ala Val
            195                 200                 205

GTG GAA AAC AGC CTG TGG CAA GGC GTA CCA AAT TAC CTG CGC GAA CTG      908
Val Glu Asn Ser Leu Trp Gln Gly Val Pro Asn Tyr Leu Arg Glu Leu
210                 215                 220

AAC GAA CAA CTG GAA GAG AAC CTC GGC TAC AAA CTG CCC GTC GAA TTT      956
Asn Glu Gln Leu Glu Glu Asn Leu Gly Tyr Lys Leu Pro Val Glu Phe
225                 230                 235                 240

GTT CCG GTC CGT TTT ACT TCG TGG ATG GGC GGC GAC CGC GAC GGC AAC     1004
Val Pro Val Arg Phe Thr Ser Trp Met Gly Gly Asp Arg Asp Gly Asn
            245                 250                 255

CCG AAC GTC ACT GCC GAT ATC ACC CGC CAC GTC CTG CTA CTC AGC CGC     1052
Pro Asn Val Thr Ala Asp Ile Thr Arg His Val Leu Leu Leu Ser Arg
            260                 265                 270

TGG AAA GCC ACC GAT TTG TTC CTG AAA GAT ATT CAG GTG CTG GTT TCT     1100
Trp Lys Ala Thr Asp Leu Phe Leu Lys Asp Ile Gln Val Leu Val Ser
            275                 280                 285

GAA CTG TCG ATG GTT GAA GCG ACC CCT GAA CTG CTG GCG CTG GTT GGC     1148
Glu Leu Ser Met Val Glu Ala Thr Pro Glu Leu Leu Ala Leu Val Gly
            290                 295                 300

GAA GAA GGT GCC GCA GAA CCG TAT CGC TAT CTG ATG AAA AAC CTG CGT     1196
Glu Glu Gly Ala Ala Glu Pro Tyr Arg Tyr Leu Met Lys Asn Leu Arg
305                 310                 315                 320

TCT CGC CTG ATG GCG ACA CAG GCA TGG CTG GAA GCG CGC CTG AAA GGC     1244
Ser Arg Leu Met Ala Thr Gln Ala Trp Leu Glu Ala Arg Leu Lys Gly
                325                 330                 335

GAA GAA CTG CCA AAA CCA GAA GGC CTG CTG ACA CAA AAC GAA GAA CTG     1292
Glu Glu Leu Pro Lys Pro Glu Gly Leu Leu Thr Gln Asn Glu Glu Leu
            340                 345                 350

TGG GAA CCG CTC TAC GCT TGC TAC CAG TCA CTT CAG GCG TGT GGC ATG     1340
Trp Glu Pro Leu Tyr Ala Cys Tyr Gln Ser Leu Gln Ala Cys Gly Met
            355                 360                 365

GGT ATT ATC GCC AAC GGC GAT CTG CTC GAC ACC CTG CGC CGC GTG AAA     1388
Gly Ile Ile Ala Asn Gly Asp Leu Leu Asp Thr Leu Arg Arg Val Lys
370                 375                 380

TGT TTC GGC GTA CCG CTG GTC CGT ATT GAT ATC CGT CAG GAG AGC ACG     1436
Cys Phe Gly Val Pro Leu Val Arg Ile Asp Ile Arg Gln Glu Ser Thr
385                 390                 395                 400

CGT CAT ACC GAA GCG CTG GGC GAG CTG ACC CGC TAC CTC GGT ATC GGC     1484
Arg His Thr Glu Ala Leu Gly Glu Leu Thr Arg Tyr Leu Gly Ile Gly
                405                 410                 415

GAC TAC GAA AGC TGG TCA GAG GCC GAC AAA CAG GCG TTC CTG ATC CGC     1532
Asp Tyr Glu Ser Trp Ser Glu Ala Asp Lys Gln Ala Phe Leu Ile Arg
            420                 425                 430

GAA CTG AAC TCC AAA CGT CCG CTT CTG CCG CGC AAC TGG CAA CCA AGC     1580
Glu Leu Asn Ser Lys Arg Pro Leu Leu Pro Arg Asn Trp Gln Pro Ser
            435                 440                 445

GCC GAA ACG CGC GAA GTG CTC GAT ACC TGC CAG GTG ATT GCC GAA GCA     1628
Ala Glu Thr Arg Glu Val Leu Asp Thr Cys Gln Val Ile Ala Glu Ala
            450                 455                 460

CCG CAA GGC TCC ATT GCC GCC TAC GTG ATC TCG ATG GCG AAA ACG CCG     1676
Pro Gln Gly Ser Ile Ala Ala Tyr Val Ile Ser Met Ala Lys Thr Pro
465                 470                 475                 480

TCC GAC GTA CTG GCT GTC CAC CTG CTG CTG AAA GAA GCG GGT ATC GGG     1724
Ser Asp Val Leu Ala Val His Leu Leu Leu Lys Glu Ala Gly Ile Gly
            485                 490                 495
```

```
TTT GCG ATG CCG GTT GCT CCG CTG TTT GAA ACC CTC GAT GAT CTG AAC      1772
Phe Ala Met Pro Val Ala Pro Leu Phe Glu Thr Leu Asp Asp Leu Asn
            500                 505                 510

AAC GCC AAC GAT GTC ATG ACC CAG CTG CTC AAT ATT GAC TGG TAT CGT      1820
Asn Ala Asn Asp Val Met Thr Gln Leu Leu Asn Ile Asp Trp Tyr Arg
            515                 520                 525

GGC CTG ATT CAG GGC AAA CAG ATG GTG ATG ATT GGC TAT TCC GAC TCA      1868
Gly Leu Ile Gln Gly Lys Gln Met Val Met Ile Gly Tyr Ser Asp Ser
530                 535                 540

GCA AAA GAT GCG GGA GTG ATG GCA GCT TCC TGG GCG CAA TAT CAG GCA      1916
Ala Lys Asp Ala Gly Val Met Ala Ala Ser Trp Ala Gln Tyr Gln Ala
545                 550                 555                 560

CAG GAT GCA TTA ATC AAA ACC TGC GAA AAA GCG GGT ATT GAG CTG ACG      1964
Gln Asp Ala Leu Ile Lys Thr Cys Glu Lys Ala Gly Ile Glu Leu Thr
                565                 570                 575

TTG TTC CAC GGT CGC GGC GGT TCC ATT GGT CGC GGC GGC GCA CCT GCT      2012
Leu Phe His Gly Arg Gly Gly Ser Ile Gly Arg Gly Gly Ala Pro Ala
            580                 585                 590

CAT GCG GCG CTG CTG TCA CAA CCG CCA GGA AGC CTG AAA GGC GGC CTG      2060
His Ala Ala Leu Leu Ser Gln Pro Pro Gly Ser Leu Lys Gly Gly Leu
            595                 600                 605

CGC GTA ACC GAA CAG GGC GAG ATG ATC CGC TTT AAA TAT GGT CTG CCA      2108
Arg Val Thr Glu Gln Gly Glu Met Ile Arg Phe Lys Tyr Gly Leu Pro
610                 615                 620

GAA ATC ACC GTC AGC AGC CTG TCG CTT TAT ACC GGG GCG ATT CTG GAA      2156
Glu Ile Thr Val Ser Ser Leu Ser Leu Tyr Thr Gly Ala Ile Leu Glu
625                 630                 635                 640

GCC AAC CTG CTG CCA CCG CCG GAG CCG AAA GAG AGC TGG CGT CGC ATT      2204
Ala Asn Leu Leu Pro Pro Pro Glu Pro Lys Glu Ser Trp Arg Arg Ile
                645                 650                 655

ATG GAT GAA CTG TCA GTC ATC TCC TGC GAT GTC TAC CGC GGC TAC GTA      2252
Met Asp Glu Leu Ser Val Ile Ser Cys Asp Val Tyr Arg Gly Tyr Val
            660                 665                 670

CGT GAA AAC AAA GAT TTT GTG CCT TAC TTC CGC TCC GCT ACG CCG GAA      2300
Arg Glu Asn Lys Asp Phe Val Pro Tyr Phe Arg Ser Ala Thr Pro Glu
            675                 680                 685

CAA GAA CTG GGC AAA CTG CCG TTG GGT TCA CGT CCG GCG AAA CGT CGC      2348
Gln Glu Leu Gly Lys Leu Pro Leu Gly Ser Arg Pro Ala Lys Arg Arg
            690                 695                 700

CCA ACC GGC GGC GTC GAG TCA CTA CGC GCC ATT CCG TGG ATC TTC GCC      2396
Pro Thr Gly Gly Val Glu Ser Leu Arg Ala Ile Pro Trp Ile Phe Ala
705                 710                 715                 720

TGG ACG CAA AAC CGT CTG ATG CTC CCC GCC TGG CTG GGT GCA GGT ACG      2444
Trp Thr Gln Asn Arg Leu Met Leu Pro Ala Trp Leu Gly Ala Gly Thr
                725                 730                 735

GCG CTG CAA AAA GTG GTC GAA GAC GGC AAA CAG AGC GAG CTG GAG GCT      2492
Ala Leu Gln Lys Val Val Glu Asp Gly Lys Gln Ser Glu Leu Glu Ala
            740                 745                 750

ATG TGC CGC GAT TGG CCA TTC TTC TCG ACG CGT CTC GGC ATG CTG GAG      2540
Met Cys Arg Asp Trp Pro Phe Phe Ser Thr Arg Leu Gly Met Leu Glu
            755                 760                 765

ATG GTC TTC GCC AAA GCA GAC CTG TGG CTG GCG GAA TAC TAT GAC CAA      2588
Met Val Phe Ala Lys Ala Asp Leu Trp Leu Ala Glu Tyr Tyr Asp Gln
            770                 775                 780

CGC CTG GTA GAC AAA GCA CTG TGG CCG TTA GGT AAA GAG TTA CGC AAC      2636
Arg Leu Val Asp Lys Ala Leu Trp Pro Leu Gly Lys Glu Leu Arg Asn
785                 790                 795                 800

CTG CAA GAA GAA GAC ATC AAA GTG GTG CTG GCG ATT GCC AAC GAT TCC      2684
Leu Gln Glu Glu Asp Ile Lys Val Val Leu Ala Ile Ala Asn Asp Ser
            805                 810                 815
```

| | | |
|---|---|---|
| CAT CTG ATG GCC GAT CTG CCG TGG ATT GCA GAG TCT ATT CAG CTA CGG<br>His Leu Met Ala Asp Leu Pro Trp Ile Ala Glu Ser Ile Gln Leu Arg<br>820 825 830 | | 2732 |
| AAT ATT TAC ACC GAC CCG CTG AAC GTA TTG CAG GCC GAG TTG CTG CAC<br>Asn Ile Tyr Thr Asp Pro Leu Asn Val Leu Gln Ala Glu Leu Leu His<br>835 840 845 | | 2780 |
| CGC TCC CGC CAG GCA GAA AAA GAA GGC CAG GAA CCG GAT CCT CGC GTC<br>Arg Ser Arg Gln Ala Glu Lys Glu Gly Gln Glu Pro Asp Pro Arg Val<br>850 855 860 | | 2828 |
| GAA CAA GCG TTA ATG GTC ACT ATT GCC GGG ATT GCG GCA GGT ATG CGT<br>Glu Gln Ala Leu Met Val Thr Ile Ala Gly Ile Ala Ala Gly Met Arg<br>865 870 875 880 | | 2876 |
| AAT ACC GGC TAA TCTTCCTCTT CTGCAAACCC TCGTGCTTTT GCGCGAGGGT<br>Asn Thr Gly | | 2928 |
| TTTCTGAAAT ACTTCTGTTC TAACACCCTC GTTTTCAATA TATTTCTGTC TGCATTTTAT | | 2988 |
| TCAAATTCTG AATATACCTT CAGATATCCT TAAGGGCCTC GTGATACGCC TATTTTTATA | | 3048 |
| GGTTAATGTC ATGATAATAA TGGTTTCTTA GACGTCAGGT GGCACTTTTC GGGGAAATGT | | 3108 |
| GCGCGGAACC CCTATTTGTT TATTTTTCTA AATACATTCA AATATGTATC CGCTCATGAG | | 3168 |
| ACAATAACCC TGATAAATGC TTCAATAATA TTGAAAAAGG AAGAGTATGA GTATTCAACA | | 3228 |
| TTTCCGTGTC GCCCTTATTC CCTTTTTTGC GGCATTTTGC CTTCCTGTTT TTGCTCACCC | | 3288 |
| AGAAACGCTG GTGAAAGTAA AAGATGCTGA AGATCAGTTG GGTGCACGAG TGGGTTACAT | | 3348 |
| CGAACTGGAT CTCAACAGCG GTAAGATCCT TGAGAGTTTT CGCCCCGAAG AACGTTTTCC | | 3408 |
| AATGATGAGC ACTTTTAAAG TTCTGCTATG TGGCGCGGTA TTATCCCGTA TTGACGCCGG | | 3468 |
| GCAAGAGCAA CTCGGTCGCC GCATACACTA TTCTCAGAAT GACTTGGTTG AGTACTCACC | | 3528 |
| AGTCACAGAA AAGCATCTTA CGGATGGCAT GACAGTAAGA GAATTATGCA GTGCTGCCAT | | 3588 |
| AACCATGAGT GATAACACTG CGGCCAACTT ACTTCTGACA ACGATCGGAG GACCGAAGGA | | 3648 |
| GCTAACCGCT TTTTTGCACA ACATGGGGGA TCATGTAACT CGCCTTGATC GTTGGGAACC | | 3708 |
| GGAGCTGAAT GAAGCCATAC CAAACGACGA GCGTGACACC ACGATGCCTG TAGCAATGGC | | 3768 |
| AACAACGTTG CGCAAACTAT TAACTGGCGA ACTACTTACT CTAGCTTCCC GGCAACAATT | | 3828 |
| AATAGACTGG ATGGAGGCGG ATAAAGTTGC AGGACCACTT CTGCGCTCGG CCCTTCCGGC | | 3888 |
| TGGCTGGTTT ATTGCTGATA AATCTGGAGC CGGTGAGCGT GGGTCTCGCG GTATCATTGC | | 3948 |
| AGCACTGGGG CCAGATGGTA AGCCCTCCCG TATCGTAGTT ATCTACACGA CGGGGAGTCA | | 4008 |
| GGCAACTATG GATGAACGAA ATAGACAGAT CGCTGAGATA GGTGCCTCAC TGATTAAGCA | | 4068 |
| TTGGTAACTG TCAGACCAAG TTTACTCATA TATACTTTAG ATTGATTTAA AACTTCATTT | | 4128 |
| TTAATTTAAA AGGATCTAGG TGAAGATCCT TTTTGATAAT CTCATGACCA AAATCCCTTA | | 4188 |
| ACGTGAGTTT TCGTTCCACT GAGCGTCAGA CCCCGTAGAA AAGATCAAAG GATCTTCTTG | | 4248 |
| AGATCCTTTT TTTCTGCGCG TAATCTGCTG CTTGCAAACA AAAAAACCAC CGCTACCAGC | | 4308 |
| GGTGGTTTGT TTGCCGGATC AAGAGCTACC AACTCTTTTT CCGAAGGTAA CTGGCTTCAG | | 4368 |
| CAGAGCGCAG ATACCAAATA CTGTCCTTCT AGTGTAGCCG TAGTTAGGCC ACCACTTCAA | | 4428 |
| GAACTCTGTA GCACCGCCTA CATACCTCGC TCTGCTAATC CTGTTACCAG TGGCTGCTGC | | 4488 |
| CAGTGGCGAT AAGTCGTGTC TTACCGGGTT GGACTCAAGA CGATAGTTAC CGGATAAGGC | | 4548 |
| GCAGCGGTCG GGCTGAACGG GGGGTTCGTG CACACAGCCC AGCTTGGAGC GAACGACCTA | | 4608 |
| CACCGAACTG AGATACCTAC AGCGTGAGCA TTGAGAAAGC GCCACGCTTC CCGAAGGGAG | | 4668 |
| AAAGGCGGAC AGGTATCCGG TAAGCGGCAG GGTCGGAACA GGAGAGCGCA CGAGGGAGCT | | 4728 |
| TCCAGGGGGA AACGCCTGGT ATCTTTATAG TCCTGTCGGG TTTCGCCACC TCTGACTTGA | | 4788 |

```
GCGTCGATTT TTGTGATGCT CGTCAGGGGG GCGGAGCCTA TGGAAAAACG CCAGCAACGC       4848

GGCCTTTTTA CGGTTCCTGG CCTTTTGCTG GCCTTTTGCT CACATGTTCT TTCCTGCGTT       4908

ATCCCCTGAT TCTGTGGATA ACCGTATTAC CGCCTTTGAG TGAGCTGATA CCGCTCGCCG       4968

CAGCCGAACG ACCGAGCGCA GCGAGTCAGT GAGCGAGGAA GCGGAAGAGC GCCCAATACG       5028

CAAACCGCCT CTCCCCGCGC GTTGGCCGAT TCATTAATGC AGAAGGGTTG GTTTGCGCAT       5088

TCACAGTTCT CCGCAAGAAT TGATTGGCTC CAATTCTTGG AGTGGTGAAT CCGTTAGCGA       5148

GGTGCCGCCG GCTTCCATTC AGGTCGAGGT GGCCCGGG                              5186
```

(2) INFORMATION FOR SEQ ID NO:2:

(i) SEQUENCE CHARACTERISTICS:
        (A) LENGTH: 883 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asn Glu Gln Tyr Ser Ala Leu Arg Ser Asn Val Ser Met Leu Gly
  1               5                  10                  15

Lys Val Leu Gly Glu Thr Ile Lys Asp Ala Leu Gly Glu His Ile Leu
             20                  25                  30

Glu Arg Val Glu Thr Ile Arg Lys Leu Ser Lys Ser Ser Arg Ala Gly
         35                  40                  45

Asn Asp Ala Asn Arg Gln Glu Leu Leu Thr Thr Leu Gln Asn Leu Ser
     50                  55                  60

Asn Asp Glu Leu Leu Pro Val Ala Arg Ala Phe Ser Gln Phe Leu Asn
 65                  70                  75                  80

Leu Ala Asn Thr Ala Glu Gln Tyr His Ser Ile Ser Pro Lys Gly Glu
                 85                  90                  95

Ala Ala Ser Asn Pro Glu Val Ile Ala Arg Thr Leu Arg Lys Leu Lys
            100                 105                 110

Asn Gln Pro Glu Leu Ser Glu Asp Thr Ile Lys Lys Ala Val Glu Ser
        115                 120                 125

Leu Ser Leu Glu Leu Val Leu Thr Ala His Pro Thr Glu Ile Thr Arg
    130                 135                 140

Arg Thr Leu Ile His Lys Met Val Glu Val Asn Ala Cys Leu Lys Gln
145                 150                 155                 160

Leu Asp Asn Lys Asp Ile Ala Asp Tyr Glu His Asn Gln Leu Met Arg
                165                 170                 175

Arg Leu Arg Gln Leu Ile Ala Gln Ser Trp His Thr Asp Glu Ile Arg
            180                 185                 190

Lys Leu Arg Pro Ser Pro Val Asp Glu Ala Lys Trp Gly Phe Ala Val
        195                 200                 205

Val Glu Asn Ser Leu Trp Gln Gly Val Pro Asn Tyr Leu Arg Glu Leu
    210                 215                 220

Asn Glu Gln Leu Glu Glu Asn Leu Gly Tyr Lys Leu Pro Val Glu Phe
225                 230                 235                 240

Val Pro Val Arg Phe Thr Ser Trp Met Gly Gly Asp Arg Asp Gly Asn
                245                 250                 255

Pro Asn Val Thr Ala Asp Ile Thr Arg His Val Leu Leu Leu Ser Arg
            260                 265                 270

Trp Lys Ala Thr Asp Leu Phe Leu Lys Asp Ile Gln Val Leu Val Ser
        275                 280                 285
```

-continued

```
Glu Leu Ser Met Val Glu Ala Thr Pro Glu Leu Ala Leu Val Gly
    290                 295                 300
Glu Glu Gly Ala Ala Glu Pro Tyr Arg Tyr Leu Met Lys Asn Leu Arg
305                 310                 315                 320
Ser Arg Leu Met Ala Thr Gln Ala Trp Leu Glu Ala Arg Leu Lys Gly
                325                 330                 335
Glu Glu Leu Pro Lys Pro Glu Gly Leu Leu Thr Gln Asn Glu Glu Leu
                340                 345                 350
Trp Glu Pro Leu Tyr Ala Cys Tyr Gln Ser Leu Gln Ala Cys Gly Met
            355                 360                 365
Gly Ile Ile Ala Asn Gly Asp Leu Leu Asp Thr Leu Arg Arg Val Lys
        370                 375                 380
Cys Phe Gly Val Pro Leu Val Arg Ile Asp Ile Arg Gln Glu Ser Thr
385                 390                 395                 400
Arg His Thr Glu Ala Leu Gly Glu Leu Thr Arg Tyr Leu Gly Ile Gly
                405                 410                 415
Asp Tyr Glu Ser Trp Ser Glu Ala Asp Lys Gln Ala Phe Leu Ile Arg
                420                 425                 430
Glu Leu Asn Ser Lys Arg Pro Leu Leu Pro Arg Asn Trp Gln Pro Ser
            435                 440                 445
Ala Glu Thr Arg Glu Val Leu Asp Thr Cys Gln Val Ile Ala Glu Ala
450                 455                 460
Pro Gln Gly Ser Ile Ala Ala Tyr Val Ile Ser Met Ala Lys Thr Pro
465                 470                 475                 480
Ser Asp Val Leu Ala Val His Leu Leu Leu Lys Glu Ala Gly Ile Gly
                485                 490                 495
Phe Ala Met Pro Val Ala Pro Leu Phe Glu Thr Leu Asp Asp Leu Asn
                500                 505                 510
Asn Ala Asn Asp Val Met Thr Gln Leu Leu Asn Ile Asp Trp Tyr Arg
            515                 520                 525
Gly Leu Ile Gln Gly Lys Gln Met Val Met Ile Gly Tyr Ser Asp Ser
        530                 535                 540
Ala Lys Asp Ala Gly Val Met Ala Ala Ser Trp Ala Gln Tyr Gln Ala
545                 550                 555                 560
Gln Asp Ala Leu Ile Lys Thr Cys Glu Lys Ala Gly Ile Glu Leu Thr
                565                 570                 575
Leu Phe His Gly Arg Gly Gly Ser Ile Gly Arg Gly Gly Ala Pro Ala
            580                 585                 590
His Ala Ala Leu Leu Ser Gln Pro Pro Gly Ser Leu Lys Gly Gly Leu
            595                 600                 605
Arg Val Thr Glu Gln Gly Glu Met Ile Arg Phe Lys Tyr Gly Leu Pro
        610                 615                 620
Glu Ile Thr Val Ser Ser Leu Ser Leu Tyr Thr Gly Ala Ile Leu Glu
625                 630                 635                 640
Ala Asn Leu Leu Pro Pro Glu Pro Lys Glu Ser Trp Arg Arg Ile
                645                 650                 655
Met Asp Glu Leu Ser Val Ile Ser Cys Asp Val Tyr Arg Gly Tyr Val
            660                 665                 670
Arg Glu Asn Lys Asp Phe Val Pro Tyr Phe Arg Ser Ala Thr Pro Glu
            675                 680                 685
Gln Glu Leu Gly Lys Leu Pro Leu Gly Ser Arg Pro Ala Lys Arg Arg
        690                 695                 700
Pro Thr Gly Gly Val Glu Ser Leu Arg Ala Ile Pro Trp Ile Phe Ala
```

```
705                710                715                720
Trp Thr Gln Asn Arg Leu Met Leu Pro Ala Trp Leu Gly Ala Gly Thr
                725                730                735

Ala Leu Gln Lys Val Val Glu Asp Gly Lys Gln Ser Glu Leu Glu Ala
                740                745                750

Met Cys Arg Asp Trp Pro Phe Phe Ser Thr Arg Leu Gly Met Leu Glu
                755                760                765

Met Val Phe Ala Lys Ala Asp Leu Trp Leu Ala Glu Tyr Tyr Asp Gln
                770                775                780

Arg Leu Val Asp Lys Ala Leu Trp Pro Leu Gly Lys Glu Leu Arg Asn
785                790                795                800

Leu Gln Glu Glu Asp Ile Lys Val Val Leu Ala Ile Ala Asn Asp Ser
                805                810                815

His Leu Met Ala Asp Leu Pro Trp Ile Ala Glu Ser Ile Gln Leu Arg
                820                825                830

Asn Ile Tyr Thr Asp Pro Leu Asn Val Leu Gln Ala Glu Leu Leu His
                835                840                845

Arg Ser Arg Gln Ala Glu Lys Glu Gly Gln Glu Pro Asp Pro Arg Val
850                855                860

Glu Gln Ala Leu Met Val Thr Ile Ala Gly Ile Ala Ala Gly Met Arg
865                870                875                880

Asn Thr Gly
```

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(iii) HYPOTHETICAL: NO (xi) SEQUENCE DESCRIPTION: SEQ ID NO:3:

TCGCGAAGTA GCACCTGTCA CTT                                      23

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(iii) HYPOTHETICAL: NO (xi) SEQUENCE DESCRIPTION: SEQ ID NO:4:

ACGGAATTCA ATCTTACGGC C                                       21

(2) INFORMATION FOR SEQ ID NO:5:

(i) SEQUENCE CHARACTERISTICS:
        (A) LENGTH: 1643 base pairs
        (B) TYPE: nucleic acid
        (C) STRANDEDNESS: double
        (D) TOPOLOGY: linear (ii) MOLECULE TYPE: DNA (genomic)

5,919,694

37

38

-continued (vi) ORIGINAL SOURCE:
    (A) ORGANISM: Corynebacterium glutamicum
    (B) STRAIN: ATCC13869

(ix) FEATURE:
    (A) NAME/KEY: mat_peptide
    (B) LOCATION: 217..1482

(xi) SEQUENCE DESCRIPTION: SEQ ID NO:5:

```
TCGCGAAGTA GCACCTGTCA CTTTTGTCTC AAATATTAAA TCGAATATCA ATATACGGTC      60

TGTTTATTGG AACGCATCCC AGTGGCTGAG ACGCATCCGC TAAAGCCCCA GGAACCCTGT     120

GCAGAAAGAA AACACTCCTC TGGCTAGGTA GACACAGTTT ATAAAGGTAG AGTTGAGCGG     180

GTAACTGTCA GCACGTAGAT CGAAAGGTGC ACAAAG GTG GCC CTG GTC GTA CAG      234
                                        Met Ala Leu Val Val Gln
                                          1               5

AAA TAT GGC GGT TCC TCG CTT GAG AGT GCG GAA CGC ATT AGA AAC GTC      282
Lys Tyr Gly Gly Ser Ser Leu Glu Ser Ala Glu Arg Ile Arg Asn Val
             10                  15                  20

GCT GAA CGG ATC GTT GCC ACC AAG AAG GCT GGA AAT GAT GTC GTG GTT      330
Ala Glu Arg Ile Val Ala Thr Lys Lys Ala Gly Asn Asp Val Val Val
         25                  30                  35

GTC TGC TCC GCA ATG GGA GAC ACC ACG GAT GAA CTT CTA GAA CTT GCA      378
Val Cys Ser Ala Met Gly Asp Thr Thr Asp Glu Leu Leu Glu Leu Ala
     40                  45                  50

GCG GCA GTG AAT CCC GTT CCG CCA GCT CGT GAA ATG GAT ATG CTC CTG      426
Ala Ala Val Asn Pro Val Pro Pro Ala Arg Glu Met Asp Met Leu Leu
 55                  60                  65                  70

ACT GCT GGT GAG CGT ATT TCT AAC GCT CTC GTC GCC ATG GCT ATT GAG      474
Thr Ala Gly Glu Arg Ile Ser Asn Ala Leu Val Ala Met Ala Ile Glu
                 75                  80                  85

TCC CTT GGC GCA GAA GCT CAA TCT TTC ACT GGC TCT CAG GCT GGT GTG      522
Ser Leu Gly Ala Glu Ala Gln Ser Phe Thr Gly Ser Gln Ala Gly Val
             90                  95                 100

CTC ACC ACC GAG CGC CAC GGA AAC GCA CGC ATT GTT GAC GTC ACA CCG      570
Leu Thr Thr Glu Arg His Gly Asn Ala Arg Ile Val Asp Val Thr Pro
         105                 110                 115

GGT CGT GTG CGT GAA GCA CTC GAT GAG GGC AAG ATC TGC ATT GTT GCT      618
Gly Arg Val Arg Glu Ala Leu Asp Glu Gly Lys Ile Cys Ile Val Ala
     120                 125                 130

GGT TTT CAG GGT GTT AAT AAA GAA ACC CGC GAT GTC ACC ACG TTG GGT      666
Gly Phe Gln Gly Val Asn Lys Glu Thr Arg Asp Val Thr Thr Leu Gly
135                 140                 145                 150

CGT GGT GGT TCT GAC ACC ACT GCA GTT GCG TTG GCA GCT GCT TTG AAC      714
Arg Gly Gly Ser Asp Thr Thr Ala Val Ala Leu Ala Ala Ala Leu Asn
                 155                 160                 165

GCT GAT GTG TGT GAG ATT TAC TCG GAC GTT GAC GGT GTG TAT ACC GCT      762
Ala Asp Val Cys Glu Ile Tyr Ser Asp Val Asp Gly Val Tyr Thr Ala
             170                 175                 180

GAC CCG CGC ATC GTT CCT AAT GCA CAG AAG CTG GAA AAG CTC AGC TTC      810
Asp Pro Arg Ile Val Pro Asn Ala Gln Lys Leu Glu Lys Leu Ser Phe
         185                 190                 195

GAA GAA ATG CTG GAA CTT GCT GCT GTT GGC TCC AAG ATT TTG GTG CTG      858
Glu Glu Met Leu Glu Leu Ala Ala Val Gly Ser Lys Ile Leu Val Leu
     200                 205                 210

CGC AGT GTT GAA TAC GCT CGT GCA TTC AAT GTG CCA CTT CGC GTA CGC      906
Arg Ser Val Glu Tyr Ala Arg Ala Phe Asn Val Pro Leu Arg Val Arg
215                 220                 225                 230

TCG TCT TAT AGT AAT GAT CCC GGC ACT TTG ATT GCC GGC TCT ATG GAG      954
Ser Ser Tyr Ser Asn Asp Pro Gly Thr Leu Ile Ala Gly Ser Met Glu
                 235                 240                 245
```

-continued

```
GAT ATT CCT GTG GAA GAA GCA GTC CTT ACC GGT GTC GCA ACC GAC AAG      1002
Asp Ile Pro Val Glu Glu Ala Val Leu Thr Gly Val Ala Thr Asp Lys
            250                 255                 260

TCC GAA GCC AAA GTA ACC GTT CTG GGT ATT TCC GAT AAG CCA GGC GAG      1050
Ser Glu Ala Lys Val Thr Val Leu Gly Ile Ser Asp Lys Pro Gly Glu
        265                 270                 275

GCT GCC AAG GTT TTC CGT GCG TTG GCT GAT GCA GAA ATC AAC ATT GAC      1098
Ala Ala Lys Val Phe Arg Ala Leu Ala Asp Ala Glu Ile Asn Ile Asp
    280                 285                 290

ATG GTT CTG CAG AAC GTC TCC TCT GTG GAA GAC GGC ACC ACC GAC ATC      1146
Met Val Leu Gln Asn Val Ser Ser Val Glu Asp Gly Thr Thr Asp Ile
295                 300                 305                 310

ACG TTC ACC TGC CCT CGC GCT GAC GGA CGC CGT GCG ATG GAG ATC TTG      1194
Thr Phe Thr Cys Pro Arg Ala Asp Gly Arg Arg Ala Met Glu Ile Leu
                315                 320                 325

AAG AAG CTT CAG GTT CAG GGC AAC TGG ACC AAT GTG CTT TAC GAC GAC      1242
Lys Lys Leu Gln Val Gln Gly Asn Trp Thr Asn Val Leu Tyr Asp Asp
            330                 335                 340

CAG GTC GGC AAA GTC TCC CTC GTG GGT GCT GGC ATG AAG TCT CAC CCA      1290
Gln Val Gly Lys Val Ser Leu Val Gly Ala Gly Met Lys Ser His Pro
        345                 350                 355

GGT GTT ACC GCA GAG TTC ATG GAA GCT CTG CGC GAT GTC AAC GTG AAC      1338
Gly Val Thr Ala Glu Phe Met Glu Ala Leu Arg Asp Val Asn Val Asn
    360                 365                 370

ATC GAA TTG ATT TCC ACC TCT GAG ATC CGC ATT TCC GTG CTG ATC CGT      1386
Ile Glu Leu Ile Ser Thr Ser Glu Ile Arg Ile Ser Val Leu Ile Arg
375                 380                 385                 390

GAA GAT GAT CTG GAT GCT GCT GCA CGT GCA TTG CAT GAG CAG TTC CAG      1434
Glu Asp Asp Leu Asp Ala Ala Ala Arg Ala Leu His Glu Gln Phe Gln
                395                 400                 405

CTG GGC GGC GAA GAC GAA GCC GTC GTT TAT GCA GGC ACC GGA CGC TAA      1482
Leu Gly Gly Glu Asp Glu Ala Val Val Tyr Ala Gly Thr Gly Arg
            410                 415                 420

AGTTTTAAAG GAGTAGTTTT ACAATGACCA CCATCGCAGT TGTTGGTGCA ACCGGCCAGG    1542

TCGGCCAGGT TATGCGCACC CTTTTGGAAG AGCGCAATTT CCCAGCTGAC ACTGTTCGTT    1602

TCTTTGCTTC CCCGCGTTCC GCAGGCCGTA AGATTGAATT C                       1643

(2) INFORMATION FOR SEQ ID NO:6:

(i) SEQUENCE CHARACTERISTICS:
        (A) LENGTH: 421 amino acids
        (B) TYPE: amino acid
        (D) TOPOLOGY: linear (ii) MOLECULE TYPE: protein (xi) SEQUENCE DESCRIPTION: SEQ ID NO:6:

Met Ala Leu Val Val Gln Lys Tyr Gly Gly Ser Ser Leu Glu Ser Ala
 1               5                  10                  15

Glu Arg Ile Arg Asn Val Ala Glu Arg Ile Val Ala Thr Lys Lys Ala
                20                  25                  30

Gly Asn Asp Val Val Val Cys Ser Ala Met Gly Asp Thr Thr Asp
            35                  40                  45

Glu Leu Leu Glu Leu Ala Ala Ala Val Asn Pro Val Pro Pro Ala Arg
        50                  55                  60

Glu Met Asp Met Leu Leu Thr Ala Gly Glu Arg Ile Ser Asn Ala Leu
    65                  70                  75                  80

Val Ala Met Ala Ile Glu Ser Leu Gly Ala Glu Ala Gln Ser Phe Thr
                85                  90                  95
```

```
Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
    290                 295                 300

Asp Gly Thr Thr Asp Ile Thr Phe Thr Cys Pro Arg Ala Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
        355                 360                 365

Arg Asp Val Asn Val Asn Ile Glu Leu Ile Ser Thr Ser Glu Ile Arg
    370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
            420

(2) INFORMATION FOR SEQ ID NO:7:

(i) SEQUENCE CHARACTERISTICS:
        (A) LENGTH: 1643 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Corynebacterium glutamicum
        (B) STRAIN: ATCC13869

(ix) FEATURE:
```

(A) NAME/KEY: mat_peptide
(B) LOCATION: 964..1482

(xi) SEQUENCE DESCRIPTION: SEQ ID NO:7:

```
TCGCGAAGTA GCACCTGTCA CTTTTGTCTC AAATATTAAA TCGAATATCA ATATACGGTC     60

TGTTTATTGG AACGCATCCC AGTGGCTGAG ACGCATCCGC TAAAGCCCCA GGAACCCTGT    120

GCAGAAAGAA AACACTCCTC TGGCTAGGTA GACACAGTTT ATAAAGGTAG AGTTGAGCGG    180

GTAACTGTCA GCACGTAGAT CGAAAGGTGC ACAAGGTGG CCCTGGTCGT ACAGAAATAT     240

GGCGGTTCCT CGCTTGAGAG TGCGGAACGC ATTAGAAACG TCGCTGAACG GATCGTTGCC    300

ACCAAGAAGG CTGGAAATGA TGTCGTGGTT GTCTGCTCCG CAATGGGAGA CACCACGGAT    360

GAACTTCTAG AACTTGCAGC GGCAGTGAAT CCCGTTCCGC CAGCTCGTGA AATGGATATG    420

CTCCTGACTG CTGGTGAGCG TATTTCTAAC GCTCTCGTCG CCATGGCTAT TGAGTCCCTT    480

GGCGCAGAAG CTCAATCTTT CACTGGCTCT CAGGCTGGTG TGCTCACCAC CGAGCGCCAC    540

GGAAACGCAC GCATTGTTGA CGTCACACCG GGTCGTGTGC GTGAAGCACT CGATGAGGGC    600

AAGATCTGCA TTGTTGCTGG TTTTCAGGGT GTTAATAAAA AAACCCGCGA TGTCACCACG    660

TTGGGTCGTG GTGGTTCTGA CACCACTGCA GTTGCGTTGG CAGCTGCTTT GAACGCTGAT    720

GTGTGTGAGA TTTACTCGGA CGTTGACGGT GTGTATACCG CTGACCCGCG CATCGTTCCT    780

AATGCACAGA AGCTGGAAAA GCTCAGCTTC GAAGAAATGC TGGAACTTGC TGCTGTTGGC    840

TCCAAGATTT TGGTGCTGCG CAGTGTTGAA TACGCTCGTG CATTCAATGT GCCACTTCGC    900

GTACGCTCGT CTTATAGTAA TGATCCCGGC ACTTTGATTG CCGGCTCTAT GGAGGATATT    960

CCT GTG GAA GAA GCA GTC CTT ACC GGT GTC GCA ACC GAC AAG TCC GAA     1008
Met Glu Glu Ala Val Leu Thr Gly Val Ala Thr Asp Lys Ser Glu
  1               5                  10                  15

GCC AAA GTA ACC GTT CTG GGT ATT TCC GAT AAG CCA GGC GAG GCT GCC     1056
Ala Lys Val Thr Val Leu Gly Ile Ser Asp Lys Pro Gly Glu Ala Ala
              20                  25                  30

AAG GTT TTC CGT GCG TTG GCT GAT GCA GAA ATC AAC ATT GAC ATG GTT     1104
Lys Val Phe Arg Ala Leu Ala Asp Ala Glu Ile Asn Ile Asp Met Val
          35                  40                  45

CTG CAG AAC GTC TCC TCT GTG GAA GAC GGC ACC ACC GAC ATC ACG TTC     1152
Leu Gln Asn Val Ser Ser Val Glu Asp Gly Thr Thr Asp Ile Thr Phe
      50                  55                  60

ACC TGC CCT CGC GCT GAC GGA CGC CGT GCG ATG GAG ATC TTG AAG AAG     1200
Thr Cys Pro Arg Ala Asp Gly Arg Arg Ala Met Glu Ile Leu Lys Lys
 65                  70                  75

CTT CAG GTT CAG GGC AAC TGG ACC AAT GTG CTT TAC GAC GAC CAG GTC     1248
Leu Gln Val Gln Gly Asn Trp Thr Asn Val Leu Tyr Asp Asp Gln Val
 80                  85                  90                  95

GGC AAA GTC TCC CTC GTG GGT GCT GGC ATG AAG TCT CAC CCA GGT GTT     1296
Gly Lys Val Ser Leu Val Gly Ala Gly Met Lys Ser His Pro Gly Val
                100                 105                 110

ACC GCA GAG TTC ATG GAA GCT CTG CGC GAT GTC AAC GTG AAC ATC GAA     1344
Thr Ala Glu Phe Met Glu Ala Leu Arg Asp Val Asn Val Asn Ile Glu
            115                 120                 125

TTG ATT TCC ACC TCT GAG ATC CGC ATT TCC GTG CTG ATC CGT GAA GAT     1392
Leu Ile Ser Thr Ser Glu Ile Arg Ile Ser Val Leu Ile Arg Glu Asp
        130                 135                 140

GAT CTG GAT GCT GCT GCA CGT GCA TTG CAT GAG CAG TTC CAG CTG GGC     1440
Asp Leu Asp Ala Ala Ala Arg Ala Leu His Glu Gln Phe Gln Leu Gly
    145                 150                 155

GGC GAA GAC GAA GCC GTC GTT TAT GCA GGC ACC GGA CGC TAA             1482
Gly Glu Asp Glu Ala Val Val Tyr Ala Gly Thr Gly Arg
160                 165                 170
```

```
AGTTTTAAAG GAGTAGTTTT ACAATGACCA CCATCGCAGT TGTTGGTGCA ACCGGCCAGG        1542

TCGGCCAGGT TATGCGCACC CTTTTGGAAG AGCGCAATTT CCCAGCTGAC ACTGTTCGTT        1602

TCTTTGCTTC CCCGCGTTCC GCAGGCCGTA AGATTGAATT C                            1643
```

(2) INFORMATION FOR SEQ ID NO:8:

(i) SEQUENCE CHARACTERISTICS:
        (A) LENGTH: 172 amino acids
        (B) TYPE: amino acid
        (D) TOPOLOGY: linear (ii) MOLECULE TYPE: protein (xi) SEQUENCE DESCRIPTION: SEQ ID NO:8:

```
Val Glu Glu Ala Val Leu Thr Gly Val Ala Thr Asp Lys Ser Glu Ala
 1               5                  10                  15

Lys Val Thr Val Leu Gly Ile Ser Asp Lys Pro Gly Glu Ala Ala Lys
            20                  25                  30

Val Phe Arg Ala Leu Ala Asp Ala Glu Ile Asn Ile Asp Met Val Leu
        35                  40                  45

Gln Asn Val Ser Ser Val Glu Asp Gly Thr Thr Asp Ile Thr Phe Thr
    50                  55                  60

Cys Pro Arg Ala Asp Gly Arg Arg Ala Met Glu Ile Leu Lys Lys Leu
65                  70                  75                  80

Gln Val Gln Gly Asn Trp Thr Asn Val Leu Tyr Asp Asp Gln Val Gly
                85                  90                  95

Lys Val Ser Leu Val Gly Ala Gly Met Lys Ser His Pro Gly Val Thr
            100                 105                 110

Ala Glu Phe Met Glu Ala Leu Arg Asp Val Asn Val Asn Ile Glu Leu
        115                 120                 125

Ile Ser Thr Ser Glu Ile Arg Ile Ser Val Leu Ile Arg Glu Asp Asp
    130                 135                 140

Leu Asp Ala Ala Ala Arg Ala Leu His Glu Gln Phe Gln Leu Gly Gly
145                 150                 155                 160

Glu Asp Glu Ala Val Val Tyr Ala Gly Thr Gly Arg
                165                 170
```

(2) INFORMATION FOR SEQ ID NO:9:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(iii) HYPOTHETICAL: NO (xi) SEQUENCE DESCRIPTION: SEQ ID NO:9:

```
AAAAACCTGC GTTCTC                                                          16
```

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid

```
          (A) DESCRIPTION: /desc = "Synthetic DNA"

(iii) HYPOTHETICAL: NO (xi) SEQUENCE DESCRIPTION: SEQ ID NO:10:

TGACTTAAGG TTTACAGGCC                                                         20

(2) INFORMATION FOR SEQ ID NO:11:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Synthetic DNA"

(iii) HYPOTHETICAL: NO (xi) SEQUENCE DESCRIPTION: SEQ ID NO:11:

ACTGAATTCC AAATGTCCGC                                                         20

(2) INFORMATION FOR SEQ ID NO:12:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Synthetic DNA"

(iii) HYPOTHETICAL: NO (xi) SEQUENCE DESCRIPTION: SEQ ID NO:12:

AAGTGCAGGC CGTTT                                                              15
```